US012216126B2

(12) United States Patent
Shimada et al.

(10) Patent No.: US 12,216,126 B2
(45) Date of Patent: Feb. 4, 2025

(54) KIT FOR PREPARING SAMPLE FOR DETECTING MONOCLONAL ANTIBODY

(71) Applicant: SHIMADZU CORPORATION, Kyoto (JP)

(72) Inventors: Takashi Shimada, Kyoto (JP); Noriko Iwamoto, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 17/455,089

(22) Filed: Nov. 16, 2021

(65) Prior Publication Data
US 2022/0137062 A1 May 5, 2022

Related U.S. Application Data

(63) Continuation of application No. 15/556,813, filed as application No. PCT/JP2015/085459 on Dec. 18, 2015, now abandoned.

(30) Foreign Application Priority Data

Mar. 10, 2015 (JP) ................................. 2015-047729

(51) Int. Cl.
G01N 33/68 (2006.01)
C12N 11/02 (2006.01)
C12Q 1/00 (2006.01)
C12Q 1/37 (2006.01)
G01N 1/10 (2006.01)
G01N 30/06 (2006.01)
G01N 30/72 (2006.01)
G01N 33/577 (2006.01)

(52) U.S. Cl.
CPC ........... G01N 33/6848 (2013.01); G01N 1/10 (2013.01); G01N 30/06 (2013.01); G01N 30/7233 (2013.01); G01N 33/577 (2013.01); C12N 11/02 (2013.01); C12Q 1/00 (2013.01); C12Q 1/37 (2013.01); G01N 2030/067 (2013.01); G01N 2333/901 (2013.01)

(58) Field of Classification Search
None
See application file for complete search history.

(56) References Cited

U.S. PATENT DOCUMENTS 10,539,571 B2   1/2020   Shimada
2016/0252522 A1  9/2016   Shimada et al.

FOREIGN PATENT DOCUMENTS

CN   105518447 A     4/2016
JP   2010-515020 A   5/2010
JP   2012-197258 A   10/2012
WO   WO 2008/079914 A1   7/2008
WO   WO 2015/033479    * 3/2015

OTHER PUBLICATIONS

Iwamoto et al. (Analyst, 2014, 139, 576) (Year: 2014).*
Shi et al. (Journal of Water Process Engineering 1 (2014) 121-138) (Year: 2014).*
Shimada et al. (J Pharm Biomed Anal. Oct. 25, 2017;145:33-39) (Year: 2017).*
Chinese Office Action issued Nov. 2, 2021 in Chinese Patent Application No. 201580077602.X (with English translation), 17 pages.
International Search Report issued Mar. 1, 2016, in PCT/JP2015/085459 filed Dec. 18, 2015.
N. Leigh Anderson et al., "Mass Spectrometric Quantitation of Peptides and Proteins Using Stable Isotope Standards and Capture by Anti-Peptide Antibodies (SISCAPA)", Journal of Proteome Research, vol. 3, No. 2, 2004, pp. 235-244.
Qianhao Min, et al., Size-selective proteolysis on mesoporous silica-based trypsin nanoreactor for low-MW proteome analysis, Chemical Communications, vol. 46, Jun. 28, 2010, pp. 6144-6146.
Fei Xu et al., Facile Trypsin Immobilization in Polymeric Membranes for Rapid, Efficient Protein Digestion, Analytical Chemistry, vol. 82, No. 24, Dec. 15, 2010, pp. 10045-10051.
Xiaotao Duan et al., "High-Throughput Method Development for Sensitive, Accurate, and reproducible Quantification of Therapeutic Monoclonal Antibodies in Tissues Using Orthogonal Array Optimization and Nano Liquid Chromatography/Selected Reaction Monitoring Mass Spectrometry", Analytical Chemistry, vol. 84,2012, pp. 4373-4382.
Noriko Iwamoto et al., "Selective detection of complementarity-determining regions of monoclonal antibody by limiting protease access to the substrate: nano-surface and molecular-orientation limited proteolysis", Analyst, Royal Society of Chemistry, vol. / 139, 2014, pp. 576-580.
"Analysis Filter Catalog 2014", Merck Millipore, 2014, pp. 17, 21 (with partial translation).
Partial European Search Report issued Jan. 4, 2019 in Patent Application No. 15884711.1, 12 pages.
Zhang, Q. et al. "Generic Automated Method for Liquid Chromatography—Multiple Reaction Monitoring Mass Spectrometry Based Monoclonal Antibody Quantitation for Preclinical Pharmacokinetic Studies" Analytical Chemistry, American Chemical Society, vol. 86, No. 17, XP55252059, 2014, pp. 8776-8784.

(Continued)

Primary Examiner — Sergio Coffa
(74) Attorney, Agent, or Firm — Oblon, McClelland, Maier & Neustadt, L.L.P.

(57) ABSTRACT

A sample preparation kit related to the present invention provides a significantly versatile analytical technique that is not affected by the diversity of antibodies, difference in species, matrix and the like. For preparing a sample to be used for detection of a monoclonal antibody through high-performance liquid chromatography-mass spectrometry (LC-MS), the kit includes a porous body for immobilizing a monoclonal antibody to be detected; nanoparticles with an immobilized protease; a reaction vessel for selectively digesting the monoclonal antibody by bringing the porous body and nanoparticles into contact; a buffer to be introduced into the reaction vessel along with the nanoparticles and porous body so that a protease reaction is carried out; and a filtration membrane to remove the porous body and nanoparticles after the proteolysis so as to extract the reaction product and the buffer.

20 Claims, 11 Drawing Sheets

Specification includes a Sequence Listing.

(56) References Cited

OTHER PUBLICATIONS

Ulbricht, M. "Advanced functional polymer membranes" Polymer, Elsevier, vol. 47, No. 7, XP028060832, 2006, pp. 2217-2262.
Combined Office Action and Search Report issued on Mar. 21, 2019 in Chinese Patent Application No. 201580077602.X (with English translation of category of cited documents) 10 pages.
Lizhen, Z. et al. "Preparation of bioactive peptides from enzymatic hydrolysate of peanut protein via membrane separation and purification", China Oils and Fats, vol. 39, No. 10, 2014, pp. 24-29 (with English Abstract).
Office Action issued Mar. 24, 2022, in corresponding Chinese Patent Application No. 201580077602.X (with English Translation), 16 pages.
Chen Wei et al., "Simultaneous Quantitative Determination of Carcinoembryonic Antigen (CEA), Alpha Fetoprotein (AFP) and Total Prostate Specific Antigen ((PSA) in Human Serum by One-step Luminex Assay", Journal of Chengdu Medical College, vol. 4, No. 1, pp. 41-45, published on Mar. 30, 2009.
Sun Jian Jun et al., "Establishment of a high-throughput detection method for strong and weak virulence of Newcastle disease virus based on the suspension chip system", Advances in Modern Biomedicine, vol. 13, No. 9, pp. 1609-1614, published on Mar. 30, 2013.
Xing Lijie, "Establishment of an immunodetection method for toxin and RTB fusion expression and antigenicity analysis", "Wanfang Database", published on Feb. 22, 2009.
Zhao Liming, "Application of Membrane Separation Technology in Food Fermentation Industry", China Textile Press, published on Jul. 31, 2011.
"Old and Middle-Aged Food and Medicinal Use Protection, Going to Hexue", Continuing Juice Beef, Buhai Science and Technology Yipa Publishing, Jan. 31, 2015.
Basic Molecular Biology (Second Edition), edited by Liu Peinan and Wu Guoli, Higher Education Press, May 1983 2nd edition, pp. 498-499 "Solid-phase radioactive rabbit disease assay", see p. 499, paragraph 2.
"Molecular Diagnostics Experiment Guide", edited by Gao Jimin, China Medical Science and Technology Press, 1st edition in Feb. 2010, "Experiment 26" on p. 88-90, see section (1)-(5) of "4Determination Methods" on p. 90.
"Frontier Technology of Molecular Biology", edited by Fang Fud, Beijing Medical University—China Union Medical University Joint Press, published in Jul. 1998, see p. 357, paragraphs 1-2.
"Hospital Clinical Laboratory Technical Operation Standard and Laboratory (Chemical) Laboratory Management Encyclopedia" No. vol. 3, edited by Hu Zhixiang, Yinsheng Video Publishing House, Aug. 2004, see p. 1116, paragraph 3.
"Practical Methods in Plant Molecular Biology and Biotechnology", by Bernard R Glick), translated by Li Rugang, Chongqing Publishing House, published in Jan. 1999, see the last paragraphs 1-3 on p. 218).

\* cited by examiner

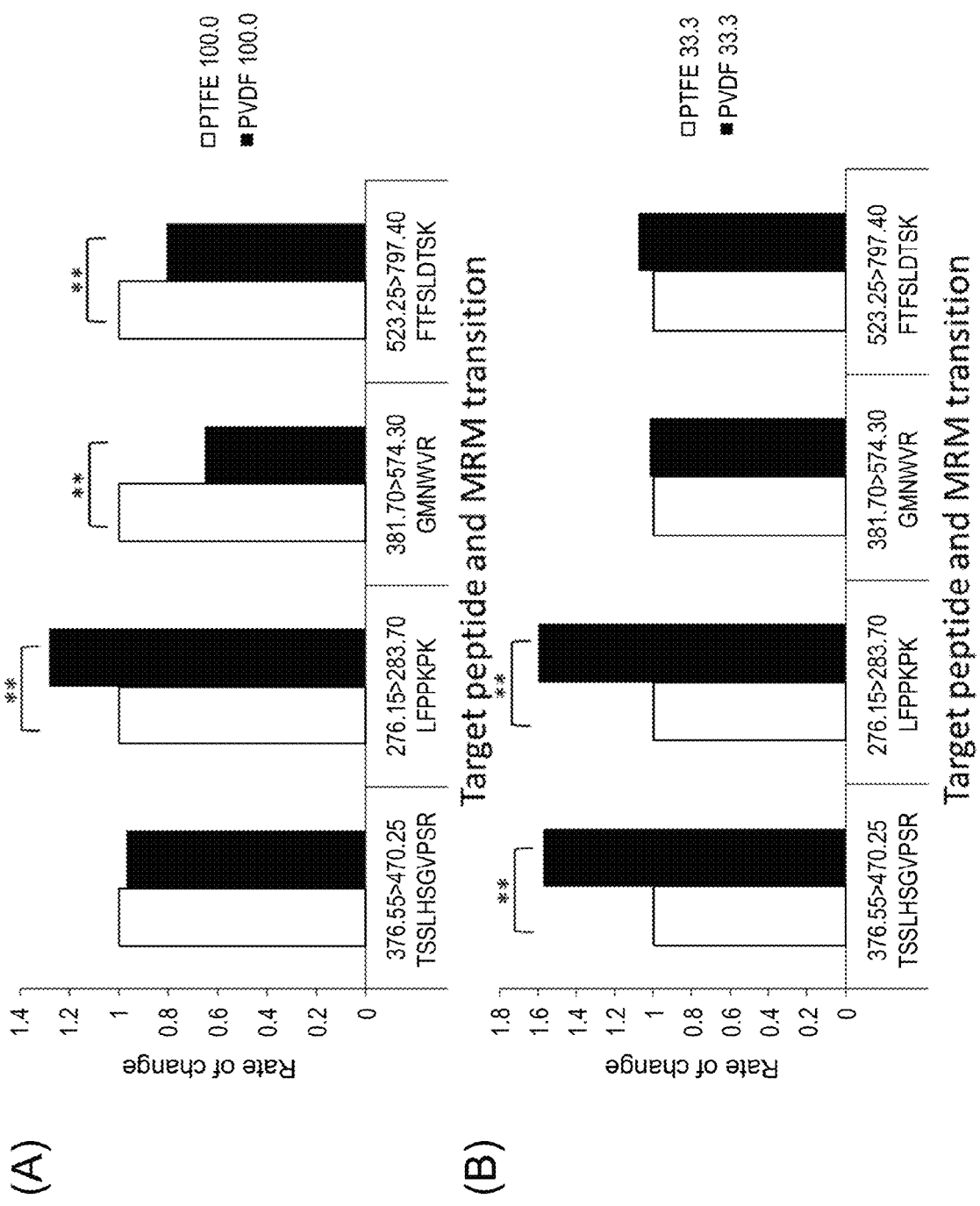

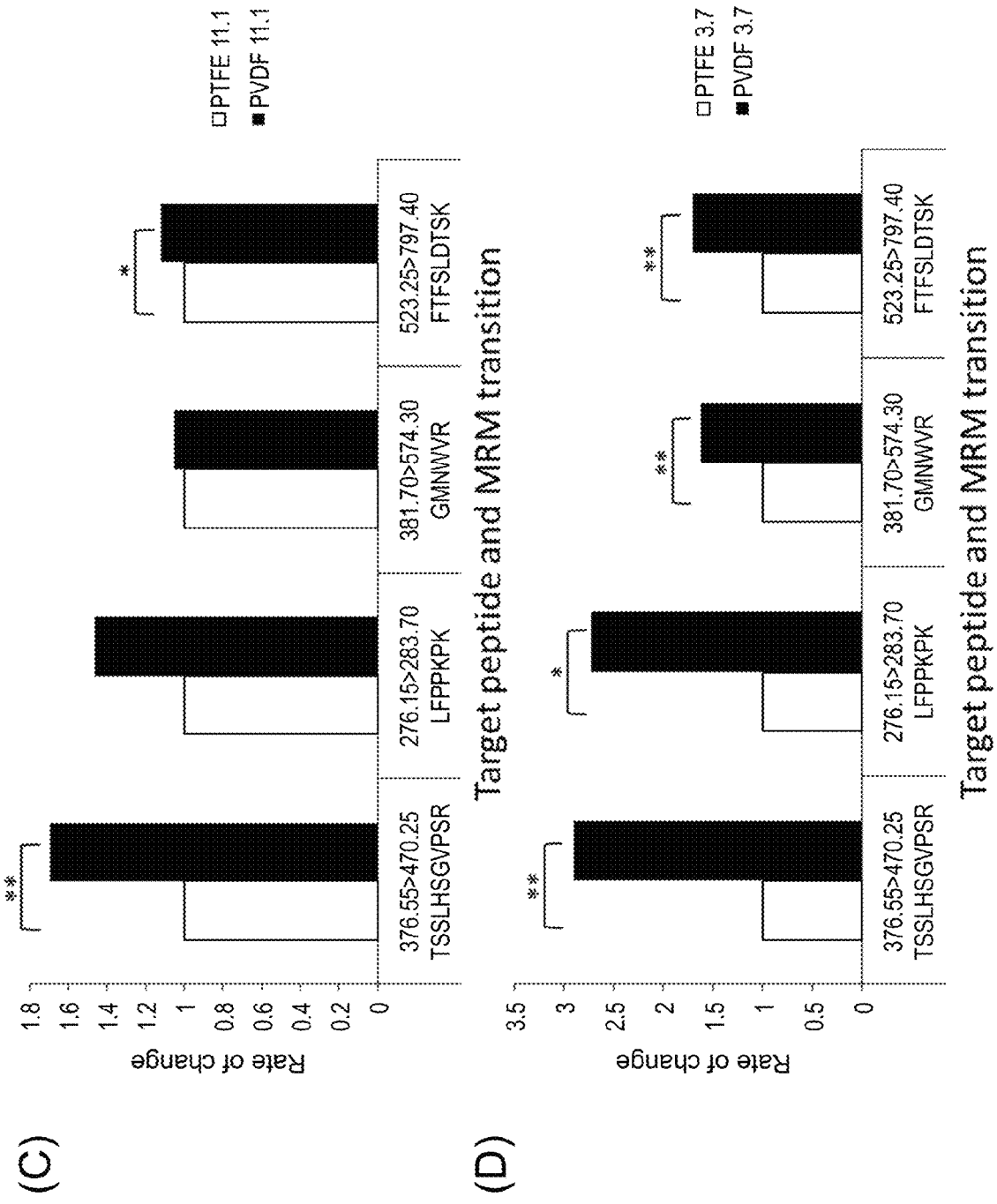

(A)

(B)

SEQUENCE LISTING

```
<160> NUMBER OF SEQ ID NOS: 47

<210> SEQ ID NO 1
<211> LENGTH: 9
<212> TYPE: PRT
<213> ORGANISM: Artificial
<220> FEATURE:
<223> OTHER INFORMATION: antibody fragment

<400> SEQUENCE: 1

Ile Tyr Pro Thr Asn Gly Tyr Thr Arg
1               5

<210> SEQ ID NO 2
<211> LENGTH: 11
<212> TYPE: PRT
<213> ORGANISM: Artificial
<220> FEATURE:
<223> OTHER INFORMATION: antibody fragment

<400> SEQUENCE: 2

Ala Glu Asp Thr Ala Val Tyr Tyr Cys Ser Arg
1               5                   10

<210> SEQ ID NO 3
<211> LENGTH: 9
<212> TYPE: PRT
<213> ORGANISM: Artificial
<220> FEATURE:
<223> OTHER INFORMATION: antibody fragment

<400> SEQUENCE: 3

Phe Thr Ile Ser Ala Asp Thr Ser Lys
1               5

<210> SEQ ID NO 4
<211> LENGTH: 11
<212> TYPE: PRT
<213> ORGANISM: Artificial
<220> FEATURE:
<223> OTHER INFORMATION: antibody fragment

<400> SEQUENCE: 4

Leu Ser Cys Ala Ala Ser Gly Phe Asn Ile Lys
1               5                   10

<210> SEQ ID NO 5
<211> LENGTH: 8
<212> TYPE: PRT
<213> ORGANISM: Artificial
<220> FEATURE:
<223> OTHER INFORMATION: antibody fragment
```

```
<400> SEQUENCE: 5

Asp Thr Tyr Ile His Trp Val Arg
1               5

<210> SEQ ID NO 6
<211> LENGTH: 7
<212> TYPE: PRT
<213> ORGANISM: Artificial
<220> FEATURE:
<223> OTHER INFORMATION: antibody fragment

<400> SEQUENCE: 6

Gly Leu Glu Trp Val Ala Arg
1               5

<210> SEQ ID NO 7
<211> LENGTH: 11
<212> TYPE: PRT
<213> ORGANISM: Artificial
<220> FEATURE:
<223> OTHER INFORMATION: antibody fragment

<400> SEQUENCE: 7

Asn Thr Ala Tyr Leu Gln Met Asn Ser Leu Arg
1               5                   10

<210> SEQ ID NO 8
<211> LENGTH: 11
<212> TYPE: PRT
<213> ORGANISM: Artificial
<220> FEATURE:
<223> OTHER INFORMATION: antibody fragment

<400> SEQUENCE: 8

Ala Glu Asp Thr Ala Val Tyr Tyr Cys Ala Lys
1               5                   10

<210> SEQ ID NO 9
<211> LENGTH: 11
<212> TYPE: PRT
<213> ORGANISM: Artificial
<220> FEATURE:
<223> OTHER INFORMATION: antibody fragment

<400> SEQUENCE: 9

Ser Thr Ala Tyr Leu Gln Met Asn Ser Leu Arg
1               5                   10

<210> SEQ ID NO 10
<211> LENGTH: 9
<212> TYPE: PRT
<213> ORGANISM: Artificial
<220> FEATURE:
<223> OTHER INFORMATION: antibody fragment

<400> SEQUENCE: 10

Phe Thr Phe Ser Leu Asp Thr Ser Lys
1               5

<210> SEQ ID NO 11
<211> LENGTH: 16
<212> TYPE: PRT
<213> ORGANISM: Artificial
<220> FEATURE:
<223> OTHER INFORMATION: antibody fragment
```

```
<400> SEQUENCE: 11

Val Leu Ile Tyr Phe Thr Ser Ser Leu His Ser Gly Val Pro Ser Arg
1               5                   10                  15

<210> SEQ ID NO 12
<211> LENGTH: 19
<212> TYPE: PRT
<213> ORGANISM: Artificial
<220> FEATURE:
<223> OTHER INFORMATION: antibody fragment

<400> SEQUENCE: 12

Leu Ser Cys Ala Ala Ser Gly Tyr Thr Phe Thr Asn Tyr Gly Met Asn
1               5                   10                  15

Trp Val Arg

<210> SEQ ID NO 13
<211> LENGTH: 7
<212> TYPE: PRT
<213> ORGANISM: Artificial
<220> FEATURE:
<223> OTHER INFORMATION: antibody fragment

<400> SEQUENCE: 13

Ala Thr Leu Thr Ala Asp Lys
1               5

<210> SEQ ID NO 14
<211> LENGTH: 6
<212> TYPE: PRT
<213> ORGANISM: Artificial
<220> FEATURE:
<223> OTHER INFORMATION: antibody fragment

<400> SEQUENCE: 14

Val Thr Met Thr Cys Arg
1               5

<210> SEQ ID NO 15
<211> LENGTH: 8
<212> TYPE: PRT
<213> ORGANISM: Artificial
<220> FEATURE:
<223> OTHER INFORMATION: antibody fragment

<400> SEQUENCE: 15

Leu Ala Ser Gly Val Pro Val Arg
1               5

<210> SEQ ID NO 16
<211> LENGTH: 12
<212> TYPE: PRT
<213> ORGANISM: Artificial
<220> FEATURE:
<223> OTHER INFORMATION: antibody fragment

<400> SEQUENCE: 16

Ala Thr Ser Asn Leu Ala Ser Gly Val Pro Val Arg
1               5                   10

<210> SEQ ID NO 17
<211> LENGTH: 16
<212> TYPE: PRT
<213> ORGANISM: Artificial
<220> FEATURE:
<223> OTHER INFORMATION: antibody fragment
```

<400> SEQUENCE: 17

Phe Ser Gly Ser Gly Ser Gly Thr Ser Tyr Ser Leu Thr Ile Ser Arg
1               5                   10                  15

<210> SEQ ID NO 18
<211> LENGTH: 15
<212> TYPE: PRT
<213> ORGANISM: Artificial
<220> FEATURE:
<223> OTHER INFORMATION: antibody fragment

<400> SEQUENCE: 18

Ala Ser Gly Tyr Thr Phe Thr Ser Tyr Asn Met His Trp Val Lys
1               5                   10                  15

<210> SEQ ID NO 19
<211> LENGTH: 14
<212> TYPE: PRT
<213> ORGANISM: Artificial
<220> FEATURE:
<223> OTHER INFORMATION: antibody fragment

<400> SEQUENCE: 19

Ala Ser Ser Ser Val Ser Tyr Ile His Trp Phe Gln Gln Lys
1               5                   10

<210> SEQ ID NO 20
<211> LENGTH: 6
<212> TYPE: PRT
<213> ORGANISM: Artificial
<220> FEATURE:
<223> OTHER INFORMATION: antibody fragment

<400> SEQUENCE: 20

Val Thr Ile Thr Cys Arg
1               5

<210> SEQ ID NO 21
<211> LENGTH: 8
<212> TYPE: PRT
<213> ORGANISM: Artificial
<220> FEATURE:
<223> OTHER INFORMATION: antibody fragment

<400> SEQUENCE: 21

Leu Tyr Ser Gly Val Pro Ser Arg
1               5

<210> SEQ ID NO 22
<211> LENGTH: 5
<212> TYPE: PRT
<213> ORGANISM: Artificial
<220> FEATURE:
<223> OTHER INFORMATION: antibody fragment

<400> SEQUENCE: 22

Ile His Trp Val Arg
1               5

<210> SEQ ID NO 23
<211> LENGTH: 11
<212> TYPE: PRT
<213> ORGANISM: Artificial
<220> FEATURE:
<223> OTHER INFORMATION: antibody fragment

```
<400> SEQUENCE: 23

Thr Thr Pro Pro Thr Phe Gly Gln Gly Thr Lys
1               5                   10

<210> SEQ ID NO 24
<211> LENGTH: 7
<212> TYPE: PRT
<213> ORGANISM: Artificial
<220> FEATURE:
<223> OTHER INFORMATION: antibody fragment

<400> SEQUENCE: 24

Ala Glu Asp Thr Ala Val Tyr
1               5

<210> SEQ ID NO 25
<211> LENGTH: 7
<212> TYPE: PRT
<213> ORGANISM: Artificial
<220> FEATURE:
<223> OTHER INFORMATION: antibody fragment

<400> SEQUENCE: 25

Leu Gln Met Asn Ser Leu Arg
1               5

<210> SEQ ID NO 26
<211> LENGTH: 6
<212> TYPE: PRT
<213> ORGANISM: Artificial
<220> FEATURE:
<223> OTHER INFORMATION: antibody fragment

<400> SEQUENCE: 26

Asp Thr Tyr Ile His Trp
1               5

<210> SEQ ID NO 27
<211> LENGTH: 7
<212> TYPE: PRT
<213> ORGANISM: Artificial
<220> FEATURE:
<223> OTHER INFORMATION: antibody fragment

<400> SEQUENCE: 27

Trp Gly Gly Asp Gly Phe Tyr
1               5

<210> SEQ ID NO 28
<211> LENGTH: 8
<212> TYPE: PRT
<213> ORGANISM: Artificial
<220> FEATURE:
<223> OTHER INFORMATION: antibody fragment

<400> SEQUENCE: 28

Leu Leu Ile Tyr Ser Ala Ser Phe
1               5

<210> SEQ ID NO 29
<211> LENGTH: 11
<212> TYPE: PRT
<213> ORGANISM: Artificial
<220> FEATURE:
<223> OTHER INFORMATION: antibody fragment

<400> SEQUENCE: 29
```

Thr Ser Ser Leu His Ser Gly Val Pro Ser Arg
1               5                   10

<210> SEQ ID NO 30
<211> LENGTH: 12
<212> TYPE: PRT
<213> ORGANISM: Artificial
<220> FEATURE:
<223> OTHER INFORMATION: antibody fragment

<400> SEQUENCE: 30

Phe Thr Ser Ser Leu His Ser Gly Val Pro Ser Arg
1               5                   10

<210> SEQ ID NO 31
<211> LENGTH: 12
<212> TYPE: PRT
<213> ORGANISM: Artificial
<220> FEATURE:
<223> OTHER INFORMATION: antibody fragment

<400> SEQUENCE: 31

Thr Gly Glu Pro Thr Tyr Ala Ala Asp Phe Lys Arg
1               5                   10

<210> SEQ ID NO 32
<211> LENGTH: 6
<212> TYPE: PRT
<213> ORGANISM: Artificial
<220> FEATURE:
<223> OTHER INFORMATION: antibody fragment

<400> SEQUENCE: 32

Gly Met Asn Trp Val Arg
1               5

<210> SEQ ID NO 33
<211> LENGTH: 16
<212> TYPE: PRT
<213> ORGANISM: Artificial
<220> FEATURE:
<223> OTHER INFORMATION: antibody fragment

<400> SEQUENCE: 33

Ile Asn Thr Tyr Thr Gly Glu Pro Thr Tyr Ala Ala Asp Phe Lys Arg
1               5                   10                  15

<210> SEQ ID NO 34
<211> LENGTH: 14
<212> TYPE: PRT
<213> ORGANISM: Artificial
<220> FEATURE:
<223> OTHER INFORMATION: antibody fragment

<400> SEQUENCE: 34

Val Thr Ile Thr Cys Ser Ala Ser Gln Asp Ile Ser Asn Tyr
1               5                   10

<210> SEQ ID NO 35
<211> LENGTH: 10
<212> TYPE: PRT
<213> ORGANISM: Artificial
<220> FEATURE:
<223> OTHER INFORMATION: antibody fragment

<400> SEQUENCE: 35

```
Val Leu Ile Tyr Phe Thr Ser Ser Leu His
1               5                   10

<210> SEQ ID NO 36
<211> LENGTH: 24
<212> TYPE: PRT
<213> ORGANISM: Artificial
<220> FEATURE:
<223> OTHER INFORMATION: antibody fragment

<400> SEQUENCE: 36

Val Thr Ile Thr Cys Ser Ala Ser Gln Asp Ile Ser Asn Tyr Leu Asn
1               5                   10                  15

Trp Tyr Gln Gln Lys Pro Gly Lys
            20

<210> SEQ ID NO 37
<211> LENGTH: 23
<212> TYPE: PRT
<213> ORGANISM: Artificial
<220> FEATURE:
<223> OTHER INFORMATION: antibody fragment

<400> SEQUENCE: 37

Gly Leu Glu Trp Val Gly Trp Ile Asn Thr Tyr Thr Gly Glu Pro Thr
1               5                   10                  15

Tyr Ala Ala Asp Phe Lys Arg
            20

<210> SEQ ID NO 38
<211> LENGTH: 7
<212> TYPE: PRT
<213> ORGANISM: Artificial
<220> FEATURE:
<223> OTHER INFORMATION: antibody fragment

<400> SEQUENCE: 38

Gly Leu Glu Trp Val Gly Trp
1               5

<210> SEQ ID NO 39
<211> LENGTH: 6
<212> TYPE: PRT
<213> ORGANISM: Artificial
<220> FEATURE:
<223> OTHER INFORMATION: antibody fragment

<400> SEQUENCE: 39

Asn Met His Trp Val Lys
1               5

<210> SEQ ID NO 40
<211> LENGTH: 12
<212> TYPE: PRT
<213> ORGANISM: Artificial
<220> FEATURE:
<223> OTHER INFORMATION: antibody fragment

<400> SEQUENCE: 40

Thr Ser Asn Pro Pro Thr Phe Gly Gly Gly Thr Lys
1               5                   10

<210> SEQ ID NO 41
<211> LENGTH: 14
<212> TYPE: PRT
<213> ORGANISM: Artificial
```

-continued

```
<220> FEATURE:
<223> OTHER INFORMATION: antibody fragment

<400> SEQUENCE: 41

Ser Gln Ser Pro Ala Ile Leu Ser Ala Ser Pro Gly Glu Lys
1               5                   10

<210> SEQ ID NO 42
<211> LENGTH: 14
<212> TYPE: PRT
<213> ORGANISM: Artificial
<220> FEATURE:
<223> OTHER INFORMATION: antibody fragment

<400> SEQUENCE: 42

Ser Thr Ser Gly Gly Thr Ala Ala Leu Gly Cys Leu Val Lys
1               5                   10

<210> SEQ ID NO 43
<211> LENGTH: 14
<212> TYPE: PRT
<213> ORGANISM: Artificial
<220> FEATURE:
<223> OTHER INFORMATION: antibody fragment

<400> SEQUENCE: 43

Ile Tyr Ala Thr Ser Asn Leu Ala Ser Gly Val Pro Val Arg
1               5                   10

<210> SEQ ID NO 44
<211> LENGTH: 12
<212> TYPE: PRT
<213> ORGANISM: Artificial
<220> FEATURE:
<223> OTHER INFORMATION: antibody fragment

<400> SEQUENCE: 44

Gly Pro Ser Val Phe Pro Leu Ala Pro Ser Ser Lys
1               5                   10

<210> SEQ ID NO 45
<211> LENGTH: 19
<212> TYPE: PRT
<213> ORGANISM: Artificial
<220> FEATURE:
<223> OTHER INFORMATION: antibody fragment

<400> SEQUENCE: 45

Gly Leu Glu Trp Ile Gly Ala Tyr Pro Gly Asn Gly Asp Thr Ser Tyr
1               5                   10                  15

Asn Gln Lys

<210> SEQ ID NO 46
<211> LENGTH: 7
<212> TYPE: PRT
<213> ORGANISM: Artificial
<220> FEATURE:
<223> OTHER INFORMATION: antibody fragment

<400> SEQUENCE: 46

Leu Phe Pro Pro Lys Pro Lys
1               5

<210> SEQ ID NO 47
<211> LENGTH: 18
<212> TYPE: PRT
```

-continued

```
<213> ORGANISM: Artificial
<220> FEATURE:
<223> OTHER INFORMATION: antibody fragment

<400> SEQUENCE: 47

Ala Ser Gln Asp Val Asn Thr Ala Val Ala Trp Tyr Gln Gln Lys Pro
1               5                   10                  15

Gly Lys
```

KIT FOR PREPARING SAMPLE FOR DETECTING MONOCLONAL ANTIBODY

CROSS-REFERENCE TO RELATED APPLICATIONS

The present application is a continuation of U.S. application Ser. No. 15/556,813, filed Sep. 8, 2017, which is a National Stage Entry of PCT/JP2015/085459, filed Dec. 18, 2015, which is based upon and claims the benefit of priority to Japanese Application No. 2015-047729, filed Mar. 10, 2015. The entire contents of these applications are incorporated herein by reference.

TECHNICAL FIELD

The present invention relates to a kit for preparing a sample for detection of a monoclonal antibody through mass spectrometry; more particularly, to such a kit that enables selective protease reaction to obtain peptide fragments containing the specific sequence of a monoclonal antibody so that even more efficient analysis is achieved.

BACKGROUND ART

The hardest challenge in drug discovery is to develop drugs capable of showing high efficacy with minor side effects. For that matter, the current focus is on pharmacokinetics, especially therapeutic drug monitoring (TDM). Whether the prescribed dosage is proper and whether the drug has reached the lesion are indicators for drug seeds to be screened so as to determine which drug seeds need to be dropped at an early stage of development. The TDM information is useful in early-stage drug discovery and clinical testing. Personalized medicine, also referred to as order-made medicine, was anticipated at one time; however, from the viewpoint of medical economics, providing personalized medical technique and medications is virtually impossible except for some wealthy patients. Accordingly, efforts are being shifted to providing available medical equipment and medications for patients who are expected to show actual therapeutic effects. Such efforts are called optimization in medicine. When developing drugs, the biggest effort in optimization in medicine is drug discovery using TDM. Especially, in applications for cancers and autoimmune disorders, discoveries of drugs called molecular targeting drugs have been in the mainstream in recent years. To determine whether molecular targeting drugs are effective, it is important for doctors to observe whether a drug has accumulated in the lesion and whether efficacy is evident at the site.

As for molecular-targeting drugs, antibody drugs targeting pathogenic proteins as their antigens are drawing more attention. Since antibodies are proteins naturally present in human bodies, fewer side effects are expected, thus making it possible to administer them at a higher concentration to enhance molecular-targeting effects. Moreover, antibody drugs are suitable in applications for cocktail therapy using multiple drugs, and reports of dramatically successful case studies have started to emerge. Furthermore, as an approach for targeted drug delivery, next-generation antibody drugs (antibody-drug conjugates) obtained by binding low-molecular anticancer agents to antibodies are already available. Also available are antibodies with efficacy enhanced by modifying sugar chains, immune checkpoint antibodies with anticancer effects obtained by activating immunocytes, and the like. Demand for antibody drugs is expected to grow even further.

Antibodies are said to naturally show significantly high molecular specificity and to accumulate in targeted lesions; however, no technology exists to prove such characteristics. Moreover, considering the issue of the pricing of antibody drugs, optimization in medicine by properly applying drugs has been discussed as to be important for patients and for medical economics. For that matter, it is important to determine levels of localization and concentration of antibody drugs so that optimal dosage is administered. Moreover, more demand is expected for quantifying concentrations of antibody drugs so as to accurately analyze efficacy indices of administered drugs for pharmacological evaluation.

The most common technique for quantifying proteins such as antibodies is called Enzyme-Linked ImmunoSorbent Assay (ELISA), which simplifies the process for quantifying the target molecule by sandwiching it between an antibody that binds to the protein of interest and the detection antibody. Since ELISA is an extremely versatile technique and its automated support system is available, ELISA is expected to become the gold standard for diagnostic techniques.

However, there are problems yet to be solved in applications of ELISA: for example, abnormal values may appear since the analyte is not directly measured; it may be time-consuming and costly since antibodies need to be labeled for each target; simultaneous detection of multiple analytes is not available; and so on. Especially, since cross-reactions with endogenous antibodies may occur when antibody drugs are used, it is hard to obtain accurate detection results. Moreover, when a neutralizing antibody and the antigen are bound, antigen recognition sites may be blocked to inhibit the use of ELISA.

Moreover, due to interspecies specificity issues, analysis conditions employed during the animal-testing phase by ELISA are often inadequate to use for testing on large animals and human beings. In other words, results need to be compared between the drug development phase and human clinical trials conducted under separate detection conditions. Since detection-inhibiting matrix components are different in ELISA for determining the drug concentration in lesional tissues, it is necessary to label multiple antibodies to perform pharmacokinetics analysis by ELISA, thereby entailing significant risks such as remarkably high cost, dropout at a later stage of development, and the like.

Meanwhile, to quantify proteins and analyze their structures using mass spectrometry, mass spectrometric techniques and various types of data analysis server/software are being developed while their application ranges are being widened remarkably. Especially, as a method that is not dependent on antibody specificity, awareness of absolute quantitation techniques using mass spectrometry is growing.

For example, when no commercial antibodies are available for a protein, purifying a large amount of such a protein used to be a necessary step for its quantification. However, using mass spectrometry eliminates the step, thus making the entire process remarkably efficient. In the field of medicine, errors of a doctor in slicing a lesion and preserving the sliced pathological section, differences in available facilities, and other issues have led to differences in immunohistochemical staining, thereby oftentimes making it difficult to determine whether the result is positive, false-positive or negative. By contrast, quantifying the target pathogenic protein in the pathological section through mass spectrometry makes it possible to determine whether the protein is a high-expression protein. Moreover, laser microdissection, a method for isolating specific cells, is universally available these days. For example, using such a method makes it possible to collect only cancer cells and to directly analyze variations in expression of pathogenic proteins through mass spectrometry. Such a process is a particularly revolutionary innovation in the field of pathology and clinical medicine, and standardization of analytical techniques is further desired.

The above process is a highly accurate analytical technique. However, to detect proteins in biological samples through mass spectrometry, target proteins often undergo protease reaction for fragmentation. Thus, it is still an important process to efficiently select peptide fragments of interest from among various peptide fragments including contaminants.

Patent Literature 1 discloses a method for detecting an antibody in a sample: in the method, F(ab')$_2$ fragments are produced by decomposing the non-immunoglobulin protein and digesting the antibody by using pepsin, and then trypsin digestion is further conducted on the fragments. In Patent Literature 2, only the peptides, properly separated through liquid chromatography prior to conducting mass spectrometry, are selected for quantification. Non-patent Literature 1 states a method for concentrating the peptide of interest using anti-peptide antibodies.

In recent years, conducting protease digestion under a microenvironment (microreactor) such as nanoparticles has drawn attention as a highly efficient technique. For example, Non-patent Literature 2 reports a method capable of selectively performing trypsin digestion on smaller molecular-weight proteins by using mesoporous silica with trypsin immobilized in pores. Non-patent Literature 3 reports an example in which trypsin is immobilized in a nylon membrane to facilitate trypsin digestion of proteins. In those methods, proteases are immobilized in the pores of porous bodies so as to react proteases on the solid-phase surface with the matrix protein in the liquid phase.

Non-patent Literature 4 proposes a high-throughput method for differentiating a monoclonal antibody from endogenous antibodies in a sample.

Kits for recovering proteins from paraffin-embedded pathological tissue sections are commercially available from Agilent Technologies, AMR, Qiagen and the like. After collecting cancer cells from pathological sections through laser microdissection, deparaffinization, extraction of proteins and digestion thereof, lesional proteins are quantified by mass spectrometry. Such a method and its clinical correlation are stated in the literature.

CITATION LIST

Patent Literature

Patent Literature 1: JP2010-515020A
Patent Literature 2: JP2012-197258A

Non-Patent Literature

Non-patent Literature 1: N. Leigh Anderson, et al., Mass Spectrometric Quantitation of Peptides and Proteins Using Stable Isotope Standards and Capture by Anti-Peptide Antibodies (SISCAPA), Journal of Proteome Research, 2004, 3(2), 235

Non-patent Literature 2: Qianhao Min, et al., Size-selective proteolysis on mesoporous silica-based trypsin nanoreactor for low-MW proteome analysis, Chemical Communications, 2010, 46, 6144

Non-patent Literature 3: Fei Xu et al., Facile Trypsin Immobilization in Polymeric Membranes for Rapid, Efficient Protein Digestion, Analytical Chemistry, Analytical Chemistry, 2010, 82, 10045

Non-patent Literature 4: Xiaotao Duan, et al., High-Throughput Method Development for Sensitive, Accurate, and Reproducible Quantification of Therapeutic Monoclonal Antibodies in Tissues Using Orthogonal Array Optimization and Nano Liquid Chromatography/Selected Reaction Monitoring Mass Spectrometry, Analytical Chemistry, 2012, 84, 4373

Non-patent Literature 5: N. Iwamoto, et al., Selective detection of complementarity determining regions of monoclonal antibody by limiting protease access to the substrate: nano-surface and molecular-orientation limited proteolysis, Analyst, 2014, 139, 576

SUMMARY OF THE INVENTION

Problems to be Solved by the Invention

To conveniently detect/quantify proteins through mass spectrometry, it is necessary to regioselectively cleave a target protein for efficiently producing peptide fragments specific to the protein while minimizing the production of other peptide fragments. Therefore, when dealing with antibodies, it is necessary to regioselectively digest the (Fab) domains, especially the variable regions of (Fab) domains, while suppressing digestion of the (Fc) domains.

The inventors of the present invention along with other researchers successfully achieved regioselective protease reaction of a monoclonal antibody by immobilizing both a protease and the substrate of antibody in a solid phase (Non-patent Literature 5: N. Iwamoto, et al., Selective detection of complementarity determining regions of a monoclonal antibody by limiting protease access to the substrate: nano-surface and molecular-orientation limited proteolysis, Analyst, 2014, 139, 576). In the method, a porous body with the monoclonal antibody immobilized in its pores and nanoparticles with an immobilized protease are brought into contact in a liquid so that the monoclonal antibody is selectively digested by the protease; and the obtained peptide fragments are detected by liquid chromatography-mass spectrometry (LC-MS). As for a protease, double digestion using trypsin and lysyl endopeptidase (Lys-C) at a ratio of 9:1 is reported to be most efficient.

The above method is revolutionary in that a monoclonal antibody is selectively digested by a protease through a solid phase-solid phase reaction. However, the method has problems yet to be solved for actual use.

The objective of the present invention is to provide a sample preparation kit capable of offering highly versatile analytical techniques regardless of diverse antibodies, interspecies differences, matrixes and the like.

Solutions to the Problems

In consideration of the above-identified problems, to allow highly accurate yet simplified analyses without depending on the skill of the user, the inventors of the present invention have conducted intense studies on various conditions for forming peptides to be detected by mass spectrometry so as to offer a kit that satisfies optimal conditions. Accordingly, the present invention has been completed.

Namely, the present invention includes the following aspects.

(1) A kit for preparing a sample for detection of a monoclonal antibody through high-performance liquid chromatography-mass spectrometry (LC-MS), including:
- a porous body for immobilizing a monoclonal antibody to be detected;
- nanoparticles with an immobilized protease;
- a reaction vessel for selectively digesting the monoclonal antibody by bringing the porous body and nanoparticles into contact;
- a buffer to be introduced into the reaction vessel along with the nanoparticles and porous body so that a protease reaction is carried out; and
- a filtration membrane to remove the porous body and nanoparticles after the proteolysis so as to extract the proteolysed product and the buffer.

(2) The kit according to (1), in which the filtration membrane hardly permeates the buffer and the peptide produced through the protease reaction under conditions where no pressure or centrifugal force is applied, but permeates the buffer and peptide under conditions where pressure or centrifugal force is applied.

(3) The kit according to (1) or (2), in which the filtration membrane is made of polyvinylidene difluoride (PVDF).

(4) The kit according to any of (1)~(3) for processing multiple samples simultaneously, in which the housing material of the filtration membrane is made of polyacrylonitrile resin.

(5) The kit for detecting a monoclonal antibody through high-performance liquid chromatography-mass spectrometry (LC-MS) according to any of (1)~(4), further enclosing instructions for mass spectrometry conditions to detect a monoclonal antibody.

(6) The kit according to any of (1)~(5), further containing at least one internal standard peptide having the amino-acid sequence specific to a target monoclonal antibody.

(7) The kit according to (6), in which the target is trastuzumab, trastuzumab-DM1, bevacizumab or rituximab, and the internal standard peptide has at least one amino-acid sequence selected from among SEQ ID NO: 1~47.

(8) A computer readable recording medium, which is used in a method for detecting a monoclonal antibody conducted by bringing a porous body with a target monoclonal antibody immobilized in its pores and nanoparticles with an immobilized protease into contact with each other in a liquid so as to perform selective proteolysis of the monoclonal antibody, and by analyzing the obtained peptide fragments through high-performance liquid chromatography-mass spectrometry; the recording medium is loaded with data for executing the mass spectrometry, including data on at least a parent ion, fragment ion, expected retention time, and voltage at each quadrupole of a triple quadrupole mass spectrometer to be applied on at least one peptide obtained through proteolysis of the monoclonal antibody.

(9) A method package for detecting a monoclonal antibody through high-performance liquid chromatography-mass spectrometry, including the recording medium according to (8) and instructions for the recording medium.

(10) The recording medium according to (8) or the method package according to (9), in which the monoclonal antibody is at least one type selected from among trastuzumab, trastuzumab-DM1, bevacizumab and rituximab.

(11) The recording medium according to (8) or the method package according to (9), in which the data are for a peptide having at least one amino-acid sequence selected from among SEQ ID NO: 1~47.

The present invention is based upon and claims the benefit of priority to Japanese Application No. 2015-047729, the entire contents of which are incorporated herein by reference.

Effects of the Invention

The kit related to the present invention is used for a process to be conducted prior to liquid chromatography-mass spectrometry (especially a triple quadrupole type). Examples of a mass spectrometer applicable for practicing the present invention are LCMS-8030, LCMS-8040, LCMS-8050 and LCMS-8080 (all made by Shimadzu Corporation). In addition, to analyze the sample pretreated using the kit related to the present invention, LCMS-IT-TOF and LCMS-Q-TOF (both made by Shimadzu Corporation) may be used.

BRIEF DESCRIPTION OF THE DRAWINGS

FIG. 2-1 shows results of studying materials of a filtration membrane used for detecting digested trastuzumab fragments; to test peptide recovery rates, polytetrafluoroethylene (PTFE) and polyvinylidene difluoride (PVDF) were compared: (A) 100.0 µg/mL of trastuzumab and (B) 33.3 µg/mL of trastuzumab;

FIG. 2-2 shows results of studying materials of a filtration membrane used for detecting digested trastuzumab fragments; to test peptide recovery rates, PTFE and PVDF were compared: (C) 11.1 µg/mL of trastuzumab and (D) 3.7 µg/mL of trastuzumab;

FIG. 2-3 shows results of studying materials of a filtration membrane used for detecting digested trastuzumab fragments; to test peptide recovery rates, PTFE and PVDF were compared: (E) 1.2 µg/mL of trastuzumab and (F) 0.4 µg/mL of trastuzumab;

FIG. 3-1 shows results of studying materials of a filtration membrane used for detecting digested bevacizumab fragments; to test peptide recovery rates, PTFE and PVDF were compared: (A) 100.0 µg/mL of bevacizumab and (B) 33.3 µg/mL of bevacizumab;

FIG. 3-2 shows results of studying materials of a filtration membrane used for detecting digested bevacizumab fragments; to test peptide recovery rates, PTFE and PVDF were compared: (C) 11.1 µg/mL of bevacizumab and (D) 3.7 µg/mL of bevacizumab;

FIG. 3-3 shows results of studying materials of a filtration membrane used for detecting digested bevacizumab fragments; to test peptide recovery rates, PTFE and PVDF were compared: (E) 1.2 µg/mL of bevacizumab and (F) 0.4 µg/mL of bevacizumab;

FIG. 4-1 shows results of comparing two membrane materials (PTFE, PVDF) and three housing types to study peptide recovery rates of filtration membrane plates used for detecting multiple analytes; peptides used were (A) FTISADTSK (SEQ ID NO: 3) and (B) ASQDVNTAVAWYQQKPGK (SEQ ID NO: 47);

FIG. 4-2 shows results of comparing two membrane materials (PTFE, PVDF) and three housing types to study peptide recovery rates of filtration membrane plates used for detecting multiple analytes; peptides used were (C) GLEW-VAR (SEQ ID NO: 6) and (D) DTYIHWVR (SEQ ID NO: 5);

DETAILED DESCRIPTION OF THE EMBODIMENTS

An embodiment of the present invention is a kit for preparing a sample for detection of a monoclonal antibody through high-performance liquid chromatography-mass spectrometry (LC-MS).

The kit includes a porous body for immobilizing a target monoclonal antibody;
nanoparticles with an immobilized protease;
a reaction vessel for selectively digesting the monoclonal antibody by bringing the porous body and nanoparticles into contact;
a buffer to be introduced in the reaction vessel along with the nanoparticles and porous body so that reaction is carried out by the protease; and
a filtration membrane to remove the porous body and nanoparticles after the reaction so as to extract the reaction product and the buffer.

Figure 1:
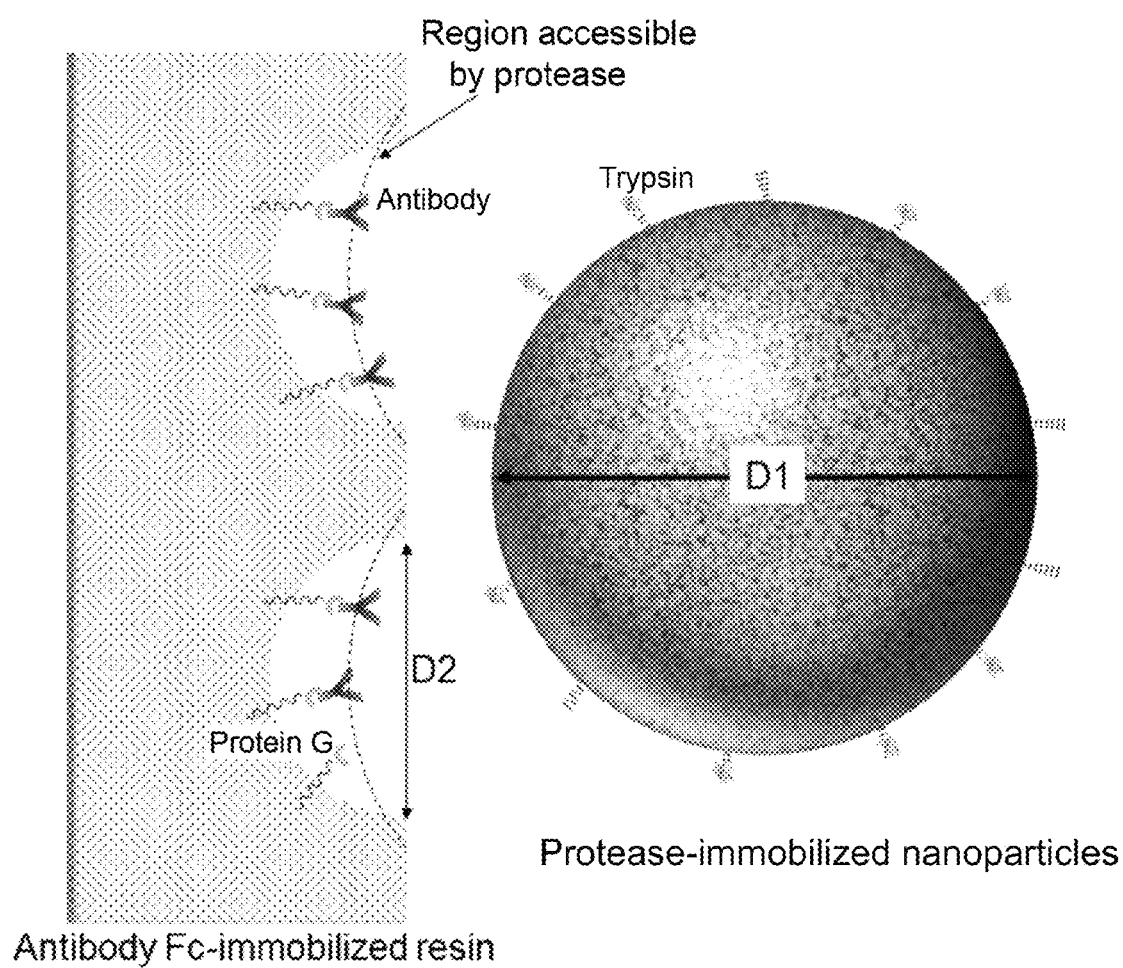
FIG. 1 shows the mechanism of a method for digesting an antibody using the kit related to the present invention.

FIG. 1 shows the mechanism of a method for digesting a monoclonal antibody using the kit related to the present invention. In the following, the present invention is described in detail by referring to the above method.

<Outline of Mass Spectrometry>

In recent years, quantification through mass spectrometry has been performed mostly by using a hybrid mass spectrometric apparatus called a triple-quadrupole mass spectrometer. More specifically, ionized biomolecules are first passed through a portion called an octopole so as to reduce the radii of intermolecular vibration of ions. Then, ions having a specific molecular weight are selected through resonance in the first quadrupole and other ions are eliminated. Such a step is also called single ion monitoring (SIM).

The selected ions are brought into the second quadrupole to be cleaved through the collision with argon. Such a cleavage reaction is called collision-induced dissociation (CID). The specific fragments produced as a result of cleavage reaction are selected in the third quadrupole so that highly sensitive and highly selective quantification is performed. Such a series of analyses is referred to as multiple reaction monitoring (MRM).

Quantification of biological samples using mass spectrometry has a maximum advantage; that is, the ability to perform quantification by setting an index on ions having structural specificity to the biomolecule. Linking mass spectrometry to high-performance liquid chromatography makes it possible to conduct consecutive analyses, which is the technical advantage found in almost none of the currently existing analytical instruments.

To detect an antibody through mass spectrometry, it is necessary to extract the antibody from biological samples such as blood and tissues and to dissolve it in an appropriate solvent. Also, since antibodies have a molecular weight that is too large to analyze the antibody as is, antibodies are decomposed by a protease into peptides, which are separated by liquid chromatography and are then subjected to mass spectrometry. The molecular weight of peptides preferable for analysis is approximately 1000 to 3000 Da.

However, when a generally known protein molecule is decomposed by a protease, approximately 100 peptide fragments are produced, and the number easily exceeds 200 when an antibody is decomposed. Therefore, even for a single protein, the number for analysis is massive, and a complex biological sample would result in an enormous number of sample sets.

In addition, sequences of antibody molecules differ only in certain portions such as CDR regions, and the rest are common to each other. Therefore, to analyze and quantify only the specific sequence of interest by selecting it from an enormous number of complex samples, rapid resolution liquid chromatography with excellent repeatability is necessary prior to conducting mass spectrometry. These days, super-fast high pressure chromatographs are available along with corresponding super-fine column resin having a uniform particle size. Using high-speed rapid resolution liquid chromatograph with a column having resistance to high pressure, separation capability is dramatically improved. However, yet further improvement is necessary for a large-scale study on proteins such as proteomics.

Also, "matrix effects" should be pointed out as issues when performing analysis through highly accurate mass spectrometry. Matrix effects indicate that when an ionization inhibitor is present or various ions are simultaneously present in the same droplet, ionization efficiency of the substance of interest is reduced. Since the energy provided for ionization is equal, an increase in substances to be ionized causes the energy to be dispersed, thus reducing the ion content.

If the number of peptides to be analyzed increases, it is difficult to completely separate them in the column. Accordingly, ionization efficiency is decreased due to matrix effects and sensitivity is lowered, thereby resulting in decreased repeatability of quantification. For that matter, high-speed channel switching functions or the like are formed on the mass-spectrometry side for improvement. However, unless the number of elements in the population is reduced, it is impossible to fundamentally overcome the matrix effects.

Considering the various aforementioned issues, the objective of the present invention is to reduce the population of an analyte while maintaining the specificity of the analyte.

<Antibody>

A monoclonal antibody is the detection target, for which a sample is prepared for detection through LC-MS by using the kit related to the present invention. A monoclonal antibody is a biopolymer made up of basic structural units, having two heavy chains (molecular weight of 50 kDa) and two light chains (molecular weight of 25 kDa) connected by disulfide bonds. In an antibody, the (Fab) domain and (Fc) domain are connected with a hinge. Heavy chains and light chains are each structured to have constant and variable regions. A constant region has a structure to maintain the Y-shape (framework structure) characteristic to antibodies, having amino-acid sequences common to most antibodies derived from the same species. On the other hand, in the variable region, there are three sites each called a complementarity-determining region (CDR) specific to each antibody. The conformation by the CDR regions (CDR1, CDR2, CDR3) is involved in the specific binding to its antigen, forming the antibody-antigen complex.

Further characterized in the conformation of an antibody are variable regions and highly flexible hinge regions compared with constant regions having a rigid structure. At the C-terminus of heavy chains, sites are known to exist for bonding with specific proteins such as protein A and protein G.

In recent years, numerous monoclonal antibodies have been developed as antibody medicines capable of working specifically on various diseases. Monoclonal antibodies to be detected are not limited specifically; examples are human antibodies such as panitumumab, ofatumumab, golimumab and ipilimumab; hominized antibodies such as tocilizumab, trastuzumab, trastuzumab-DM1, bevacizumab, omalizumab, mepolizumab, gemtuzumab, palivizumab, ranibizumab, certolizumab, ocrelizumab, mogamulizumab and eculizumab; chimeric antibodies such as rituximab, cetuximab, infliximab and basiliximab; and the like. The molecular size of a monoclonal antibody is approximately 14.5 nm.

Moreover, also included as monoclonal antibodies to be detected by the method related to the present invention is a complex obtained by adding further functionalities while maintaining the specificity of a monoclonal antibody, for example, Fc-Fusion proteins and antibody-drug conjugates (such as gemtuzumab ozogamicin and trastuzumab-emtansine). The binding of a complex may be dissociated prior to detection so that only the antibody is subjected to LC-MS, or the complex itself may be subjected to LC-MS. Based on the descriptions in the present application, any person skilled in the art should be able to set conditions optimal for the analyte when practicing the method related to the present invention.

The kit related to the present invention is designed to regioselectively perform proteolysis on the (Fab) domain of a monoclonal antibody so that the antibody is identified and quantified through mass spectrometry of the obtained peptide fragments.

<Porous Body>

As long as numerous pores are formed therein, the porous body in the kit related to the present invention is not limited to any particular type; activated carbons, porous membranes, porous resin beads, metal particles and the like may be used. Among them, those capable of regioselectively bonding with antibodies are especially preferable.

FIG. 1 shows semicircular pores, but the shape of pores is not limited particularly. It is another option to use a porous membrane with pores that penetrate through the porous body. The pore size in a porous body is not limited particularly. It is preferred to determine the size relative to the molecular size of an antibody so that when the antibody is immobilized, the site to be selectively digested is positioned near the surface layer of a pore. The average pore diameter (D2) of a porous body is appropriately set in an approximate range of 10 nm to 200 nm, which is smaller than the average particle size (D1) of nanoparticles. The average pore size (D2) of a porous body is preferred to be, for example, approximately 20 nm~200 nm, more preferably 30 nm~150 nm. To immobilize the (Fc) domain of the antibody in a pore and to regioselectively digest the (Fab) domain by a protease, the pore size of a porous body is preferred to be 30 nm~150 nm, more preferably 40 nm~120 nm, especially preferably 50 nm~100 nm, even further preferably approximately 100 nm.

In the method related to the present invention, a monoclonal antibody of interest is immobilized in the pores of a porous body. When an antibody is immobilized in pores to locate itself under a fine environment of interface between solid and liquid phases, the antibody is prone to be degenerated and the fluctuation of molecules is perturbed, making it more likely to be attacked by a protease. Also, in the present invention, since a protease is immobilized on nanoparticles as described later, the protease is sterically stable and shows low autolysis, thus increasing the stability of the protease. Accordingly, using the method related to the present invention allows the protease to maintain high activity while performing regioselective proteolysis.

In the embodiments of the present invention, it is preferred to use a porous body with pores in which linker molecules, capable of performing site-specific interactions with the antibody, are immobilized. Examples of interactions between antibodies and linker molecules are chemical bonds, hydrogen bonds, ionic bonds, complex formations, hydrophobic interactions, Van der Waals interactions, electrostatic interactions, stereoselective interactions and the like.

As for linker molecules, it is preferred to use proteins (A, G) and the like capable of making site-specific bonding with the (Fc) domains of antibodies. By using a porous body with linker molecules immobilized in its pores, the (Fc) domain of an antibody is immobilized in a pore while the (Fab) domain is located near the surface layer of the pore. Controlling the orientation of an antibody in a pore allows a protease to regioselectively digest the (Fab) domain.

The size of a linker molecule is selected so that the selective cleavage site of an antibody is located near the surface layer of a pore. The molecular size when a linker molecule is bound to an antibody is preferred to be approximately 0.5~1.5 times the pore size of the porous body, more preferably 0.6~1.2 times, even more preferably 0.7~1.1 times, especially preferably 0.8~1 times. When no linker molecule is immobilized in a porous body and the antibody is directly bound inside the pore, it is preferred for the molecular size of the antibody and the pore size of the porous body to satisfy the above relationship.

Porous bodies preferably used in the embodiments of the present invention are not limited particularly; examples are Protein G UltraLink Resin (Pierce), Toyopearl, TSKgel (Tosoh Corporation) and the like. For example, when Protein G UltraLink resin is used, 95% of the Protein G bound to the resin is known to be located inside the pores.

<Immobilization of Antibody in Porous Body>

The method for immobilizing antibodies in pores of a porous body is not limited particularly, and any method may be employed based on the characteristics between the antibody and the porous body or the linker molecule. For example, to immobilize an antibody in a porous body where protein A or G is immobilized inside a pore, it is easier to immobilize the antibody inside the pore by mixing the antibody and the buffer containing the porous body.

A porous body-to-antibody content ratio may be set appropriately. For example, for a quantitative analysis of the antibody, it is preferred for the entire amount of antibody in the sample to be immobilized in the porous body. Therefore, the ratio is preferred to be set so that an excess amount of porous body is available relative to the assumed content of the antibody in the sample.

<Nanoparticles>

Nanoparticles in a kit related to the present invention are used to immobilize a protease on their surfaces so as to control the access of the protease to an antibody immobilized inside the pores of a porous body. Accordingly, to prevent a nanoparticle from entering deep into a pore of the porous body, the average particle size (D1) of nanoparticles is set greater than the average pore size (D2) of the porous body (FIG. 1).

The shape of nanoparticles is not limited particularly, but a spherical shape is preferred so as to allow a protease to gain unified access to the pores of a porous body. In addition, nanoparticles are preferred to have a uniform particle size and to be highly dispersible.

The average particle size (D1) of nanoparticles is in a range of 50 nm~500 nm, which is preferred to be at least 1.2 times, more preferably at least 1.5 times, especially preferably at least 1.8 times (for example, approximately two times), the average pore size (D2) of a porous body. When the average pore size of a porous body is approximately 30 nm~150 nm, the average particle size (D1) of nanoparticles is preferred to be at least 100 nm, more preferably at least 150 nm. When the average pore size of a porous body is approximately 50 nm~100 nm, the average particle size of nanoparticles is preferred to be at least 120 nm, more preferably at least 150 nm, and especially preferably 170 nm. The upper limit of the average particle size (D1) of nanoparticles is preferred to be no greater than 500 nm, more preferably no greater than 300 nm to facilitate protease reaction.

The material of nanoparticles is not limited particularly as long as it is capable of immobilizing the above-mentioned protease on its surface, and is selected appropriately from metals and resins, for example. Materials prepared by coating a resin on a metal surface, or by coating a metal on a resin surface, may also be used.

Nanoparticles are preferred to be magnetic, which can be dispersed or suspended in an aquatic medium and be easily recovered from the dispersion or suspension by magnetic separation or magnetic sedimentation separation. More preferred are magnetic nanoparticles with their surfaces coated with an organic polymer since such nanoparticles are unlikely to agglomerate. The substrate of magnetic nanoparticles may be ferromagnetic alloys such as iron oxides (magnetite ($Fe_3O_4$), maghemite ($\gamma$-$Fe_2O_3$)) and ferrite ($(Fe/M)_3O_4$). The "M" in ferrite ($(Fe/M)_3O_4$) means metal ions capable of forming magnetic metal oxides when combined with iron ions; typical examples are $Co^{2+}$, $Ni^{2+}$, $Mn^{2+}$, $Mg^{2+}$, $Cu^{2+}$, $N^{2+}$ and the like. Examples of organic polymers for coating magnetic nanoparticles are polyglycidyl methacrylate (poly(GMA)), GMA-styrene copolymers, polymethyl methacrylate (PMMA), polymethyl acrylate (PMA) and the like. Specific examples of magnetic nanobeads coated with an organic polymer are FG beads, SG beads, Adembeads, nanomag and the like. As commercially available nanoparticles, FG beads made by Tamagawa Seiki Co., Ltd. (polymer magnetic nanoparticles with an approximate particle size of 200 nm produced by coating ferrite particles with polyglycidyl methacrylate (poly(GMA)) are preferred.

To immobilize a protease while suppressing adsorption of nonspecific proteins, the above nanoparticles are preferred to be modified with spacer molecules capable of bonding with the protease. When a protease is immobilized via a spacer molecule, the protease is unlikely to be separated from the nanoparticle surface, and regioselective proteolysis by the protease is thereby enhanced. Moreover, regioselectivity by a protease is enhanced when the molecular size of a spacer is adjusted so that the protease selectively makes an access to the desired site of an antibody.

A spacer is preferred to be bondable with a protease, and to be a type that does not inactivate the protease. To control the accessible range of a protease immobilized on nanoparticle surfaces, a spacer is preferred to have a smaller molecular size. The molecular size of a spacer is preferred to be no greater than 5 nm, more preferably no greater than 3 nm, even more preferably no greater than 2 nm. The molecular weight of a spacer is preferred to be 2000 or less, more preferably 1500 or less, even more preferably 1000 or less.

Spacer molecules having the above molecular size and capability of immobilizing a protease are preferred to be a non-protein type, preferably a type having a functional group on the terminus, for example, amino group, carboxyl group, ester group, epoxy group, tosyl group, hydroxyl group, thiol group, aldehyde group, maleimide group, succinimide group, azide group, biotin, avidin, chelate or the like. For example, to immobilize trypsin, spacer molecules having an activated ester group are preferred. In addition, for the arm portions excluding the functional group in the spacer, hydrophilic molecules may be attached; examples are polyethylene glycol and its derivatives, polypropylene glycol and its derivatives, polyacrylamide and its derivatives, polyethyleneimine and its derivatives, poly(ethylene oxide) and its derivatives, poly(ethylene terephthalate) and its derivatives and the like.

Nanoparticles that are surface-modified with spacer molecules are also commercially available. For example, nanoparticles surface-modified with spacer molecules having an ester group activated by N-hydroxysuccinimide (activated ester group) are sold as a product name "FG beads NETS" (Tamagawa Seiki Co., Ltd.). FG beads NETS have an approximate particle size of 200 nm±20 nm and are significantly homogeneous.

A kit related to the present invention is preferred to contain the above nanoparticles with an immobilized protease. However, it is an option to provide nanoparticles and a protease individually with an instruction for immobilizing the protease prior to using the kit.

<Protease>

In the method related to the present invention, an antibody immobilized in a pore of a porous body is cleaved at a specific amino-acid sequence site by a protease so as to produce peptide fragments.

A protease may be included in a kit separately from nanoparticles or by being immobilized on surfaces of nanoparticles.

In the embodiments of the present invention, a protease to be immobilized on nanoparticles is not limited particularly and may be appropriately selected according to the type of protein to be quantified or identified through mass spectrometry. Examples are trypsin, chymotrypsin, lysyl endopeptidase, V8 protease, AspN protease (Asp-N), ArgC protease (Arg-C), papain, pepsin, dipeptidyl peptidase and the like. They may also be used in combination thereof.

Among those on the above list, trypsin is especially preferred to be used in the embodiments of the present invention. Trypsin has a high substrate specificity, and Lys or Arg at the C-terminus of peptides after cleavage contributes to setting the charge amount and charge localization to be homogeneous. Therefore, trypsin is especially preferable when preparing samples for mass spectrometry. In addition, trypsin has a small molecular size (approximately 3.8 nm) and has active sites inside molecules. Accordingly, the region of an antibody accessible by the active site is limited, thereby enhancing the regioselectivity of proteolysis.

To provide peptide fragments for mass spectrometry as a detection sample after protease reaction of an antibody, it is preferred to use a low autolytic protease having high selectivity for the sequence to be cleaved. When using a commercially available protease, mass spectrometry-grade or sequencing-grade proteases are preferred. For example, native trypsins derived from living organisms are known to have low selectivity for cleavage sites, since they may be highly autolytic or may include those having a chymotrypsin-like activity. For that matter, commercially available mass spectrometry-grade trypsins have a higher resistance to autolysis obtained through a reductive methylation reaction of lysine residues.

Examples of a protease preferably used in the embodiments of the present invention are Trypsin Gold (Promega Corporation) and Trypsin TPCK-treated (Sigma-Aldrich Corporation).

<Immobilization of Protease on Nanoparticles>

The method for immobilizing a protease on nanoparticle surfaces is not limited specifically, and may be appropriately selected according to the characteristics of the protease and nanoparticles (or spacer molecules modifying the nanoparticle surfaces). For example, a protease may be immobilized on nanoparticle surfaces modified with a spacer by mixing a suspension of nanoparticles and a solution containing the protease. For immobilizing a protease on nanoparticle surfaces, amine coupling of a protease and nanoparticles through the above-listed functional groups of spacer molecules is preferred. For example, the carboxyl group on nanoparticle surfaces is esterified with N-hydroxysuccinimide (NETS) to make an activated ester group, to which the amino group of a protease is bonded. To carry out such coupling reactions, carbodiimides such as 1-ethyl-3-(3-dimethylaminopropyl)carbodiimide (EDAC), N,N'-dicyclohexylcarbodiimide (DCC) and bis(2,6-diisopropylphenyl) carbodiimide (DIPC) may be used in the presence of a condensing agent. Also, the amino group of a protease may be bonded with the amino group on nanoparticle surfaces by using crosslinking agents such as glutaraldehyde, bifunctional succinimide, bis(sulfosuccinimidyl)suberate (B S3), sulfonyl chloride, maleimide and pyridyl disulfide.

A protease may be coupled with nanoparticles through the functional group of spacer molecules in a simplified procedure by adding a protease solution to a suspension of nanoparticles and stirring the mixture under constant conditions.

After a protease is immobilized on nanoparticle surfaces, it is preferred to inactivate the active sites of nanoparticle surfaces which are not bonded with the protease. For example, if spacer molecules that are not coupled with the protease are present on nanoparticle surfaces, they may be bonded with contaminants in the sample. Accordingly, protease digestion may be affected negatively, or peptide fragments produced by protease digestion may be immobilized on nanoparticles. After the protease is immobilized, such trouble is suppressed by blocking spacer molecules that are not coupled with the protease. To inactivate the active sites not coupled with the protease, chemical modification is preferred. For example, activated ester groups are inactivated by forming amide bonds through reactions with a primary amine.

<Protease Digestion>

When a porous body with an immobilized antibody and nanoparticles with a protease immobilized on their surfaces are brought into contact in a liquid, the antibody is digested by the protease, producing peptide fragments. Here, "liquid" means a liquid phase in which a substrate (solid phase) and the enzyme (solid phase) make contact; it also indicates an aquatic medium suitable for protease digestion reactions.

In the embodiments of the present invention, conditions for protease reaction are not limited particularly, and those generally employed for protease reaction are employed appropriately. For example, protease reaction is carried out through incubation in a buffer adjusted to have a pH closer to the optimal pH of the protease at an approximate temperature of 37° C. for 1-20 hours.

The ratio is not limited particularly when mixing a porous body with an immobilized antibody and nanoparticles with a protease immobilized on their surfaces; the amount of protease may be set according to the amount of antibody. Under generally employed conditions for protease digestion, a substrate-to-protease ratio (weight ratio) is approximately 100:1~20:1. By contrast, in the embodiments of the present invention, since physical access of a protease to the antibody is controlled by the combined use of a porous body and nanoparticles, it is preferred to increase the protease amount compared with the amount for conventional protease digestion. For example, an antibody-to-protease ratio is preferred to be set approximately at 30:1~3:1, more preferably 15:1~4:1, even more preferably 10:1~5:1.

In the method related to the present invention, the antibody is digested by a protease while immobilized in a porous body. Since peptide fragments produced by protease digestion are present in a liquid phase, regioselective peptide fragments are obtained without performing the elusion or modification of the antibody. According to the method related to the present invention, regioselective peptide fragments are recovered using a method that is simplified compared with conventional methods.

More specifically, on protein G resin with a pore size of 100 nm, for example, the C-terminus of an antibody is immobilized while the variable regions of the antibody are made sure to face the liquid side. Next, a protease is immobilized on a nanoparticle surface with a particle size of 200 nm. By controlling the access of a protease to the antibody, a reaction site is formed for the antibody to selectively decompose at its variable regions. Also, using a nanoparticle surface having a significantly greater relative surface area as the protease reaction site, the chance for making contact with an antigen is increased.

The method for protease reaction is not limited particularly, but may be conducted under tapping rotation involving stirring using gentle rotation and constant tapping. "Gentle rotation" means a rotation of 3~10 rpm, for example; and "tapping" means instantaneous movements such as flicking and shocking (frequency: 1~5 times, preferably 2~4 times, per minute). By so doing, the porous body with an immobilized antibody and nanoparticles with an immobilized protease are efficiently brought into contact with each other while maintaining their dispersion, and protease reaction is thereby facilitated.

<Removing Porous Body and Nanoparticles>

To perform mass spectrometry on the peptide fragments obtained by protease reaction, it is necessary to remove the porous body and nanoparticles. Removal is conducted by filtration, centrifugation, magnetic separation, dialysis and the like on the sample after protease reaction.

When filtration is employed for removing the porous body and nanoparticles, the pore size of the filtration membrane is set in a range that prevents permeation of the porous body and nanoparticles but allows permeation of the digested peptide fragments. For example, porous bodies and nanoparticles may simply be removed by using a filtration membrane made of polyvinylidene difluoride (PVDF) (low-binding hydrophilic PVDF, pore size of 0.2 μm, Millipore), a membrane made of polytetrafluoroethylene (PTFE) (low-binding hydrophilic PTFE, pore size of 0.2 μm, Millipore) and the like. Using centrifugal filtration facilitates and simplifies the filtration process.

The type of filtration membranes is not limited particularly, but a filter-tube double structure is preferred to perform centrifugal filtration. For example, to prepare one sample, 0.2-µm membrane spin filters such as Millipore Ultrafree PVDF, 0.2 µm, and Millipore UFC30LG00 Ultrafree-C3LCR, 0.2 µm are preferred. In addition, for simultaneously preparing multiple samples, 0.2-µm membrane filtration plates such as Millipore MultiScreen PVDF, Barex, 0.2 µm may be preferably used.

To use the filtration membrane of tube-type filters, the tubes may be used as reaction vessels for protease reactions. In such a case, the reaction medium (including a buffer) containing nanoparticles with an immobilized protease and a porous body with an immobilized antibody are placed in a tube to perform protease reaction. Alternatively, the immobilization process of the antibody in a sample on a porous body is conducted in a tube, followed by a washing process, and nanoparticles with an immobilized protease are added to the tube. When people skilled in the art use a kit related to the present invention, they should be able to appropriately modify a series of procedures such as protease reactions and removal of porous bodies and nanoparticles.

<Liquid Chromatography-Mass Spectrometry (LC-MS)>

Antibodies are identified and quantified by analyzing the sample containing peptide fragments obtained as above through LC-MS.

To secure separation of peptide fragments and to enhance analytical accuracy, a sample prior to mass spectrometry is separated/concentrated by liquid chromatography (LC). When a sample is separated by LC, the eluate may be directly ionized to be provided for mass spectrometry. It is another option to analyze through LC/MS/MS or LC/MSn by combining LC and tandem mass spectrometry. Alternatively, the eluate from LC may be recovered and then provided to mass spectrometry. The column for LC is not limited particularly, and may be appropriately selected from hydrophobic columns such as C30, C18, C8 and C4 used for conventional peptide analyses, along with carriers for hydrophilic affinity chromatography.

Since mass spectrometry makes it possible to determine amino-acid sequences, it also makes it possible to determine whether peptide fragments are derived from specific proteins such as antibodies. Also, concentrations of peptide fragments in a sample are determined based on the peak intensities. In the embodiments of the present invention, since an antibody is regioselectively processed by a protease, the number of peptide fragment types contained in a sample is reduced. Accordingly, it is easier to set analysis conditions for mass spectrometry or the like. Prior to analysis, desalting, solubilization, extraction, concentration, drying and the like may be conducted on the sample if applicable.

The method for ionization in mass spectrometry is not limited particularly; examples are electron ionization (EI), chemical ionization (CI), field desorption (FD), fast atom bombardment (FAB), matrix-assisted laser desorption/ionization (MALDI), electrospray ionization (ESI) and the like. The method for analyzing ionized samples is not limited particularly and may be appropriately selected according to the ionization method employed for the sample; ionized samples are analyzed by using, for example, deflection by magnetic field, quadrupole (Q), ion trap (IT), time of flight (TOF), Fourier transform ion cyclotron resonance (FT-ICR) and the like. Using a triple quadrupole mass spectrometer or the like, MS/MS analysis and MS3 or higher multi-stage mass spectrometry are also available.

Employing the method related to the present invention is not limited to any particular instrument; examples are LCMS-8030, LCMS-8040, LCMS-8050 and LCMS-8080 (all made by Shimadzu Corporation), LCMS-IT-TOF and LCMS-Q-TOF (Shimadzu Corporation).

An existing database may be used to identify antibodies based on the results of mass spectrometry. In the embodiments of the present invention, using peptide fragments obtained by regioselective proteolysis of antibodies enhances the hit ratio during a database search and improves the accuracy of data. Moreover, by performing multistage mass spectrometry or the like, the amino-acid sequence of peptide fragments is specified, and the antibody is thereby identified. If peptide fragments are detected to have amino-acid sequences specific to a certain antibody, for example, the sequence of amino acids including the amino acid in the CDR2 region, then the antibody of interest is identified and quantified.

To identify and quantify an antibody based on the detection results, the number of amino-acid residues of the peptide to be detected is preferred to have 5-30, more preferably 7-25. If the number of amino-acid residues is too small, it is hard to distinguish them from contaminants or peptide fragments derived from other sites of the same protein, thereby causing detection errors. If the number of amino-acid residues is far too large, ionization may be hard and cause difficulty in detection or decrease in accuracy of quantification.

To quantify the concentration of an antibody, the amount of antibody is calculated based on the peak area or peak intensity of the detected peptide fragment ions (for multistage MS, fragment ions obtained by cleavage of parent ions). For example, the concentration of peptide fragments in a sample is calculated by associating its peak area with a previously obtained analytical curve (calibration curve), by comparing the peak area derived from the internal standard peptide added to the sample with the peak area derived from the sample, or the like. Based on the peptide fragment concentration, the amount and concentration of the antibody are determined.

<Sample Preparation Kit Related to the Present Invention>

The present invention relates to a kit for preparing a sample to be used in the aforementioned method for detecting a monoclonal antibody through high-performance liquid chromatography-mass spectrometry (LC-MS); the kit includes:

a porous body for immobilizing a monoclonal antibody to be detected;

nanoparticles with an immobilized protease;

a reaction vessel for selectively digesting the monoclonal antibody by bringing the porous body and nanoparticles into contact;

a buffer to be introduced into the reaction vessel along with the nanoparticles and porous body so that a protease reaction is carried out; and a filtration membrane to remove the porous body and nanoparticles after the reaction so as to extract the proteolysed product and the buffer.

While detection through mass spectrometry enables significantly accurate analysis, it is very important to prepare appropriate samples and to set proper conditions for analysis. The present invention provides a sample preparation kit for practicing the above-mentioned method so that accurate detection results are achieved by further simplified procedures in clinical settings, for example.

Porous bodies and nanoparticles in a kit related to the present invention are described above. As for a reaction vessel, it is not limited to any particular type, as long as it is capable of bringing the monoclonal antibody immobilized in a porous body and a protease immobilized on nanoparticles into contact with each other in a liquid phase. Since the kit is to prepare a sample for mass spectrometric detection, microtubes and plates are preferred. Those skilled in the art should be able to select an appropriate reaction vessel after considering reaction steps such as a mixing step using a vortex mixer or rotator, a filtration step for separating the obtained peptide fragments from the porous body and nanoparticles, and so on.

The buffer in a kit related to the present invention is introduced in the above-mentioned reaction vessel along with the nanoparticles and porous body for protease reactions so that the buffer provides appropriate reaction conditions. Reaction conditions are appropriately employed according to the protease, and the composition of a buffer is determined accordingly.

A kit related to the present invention also includes a filtration membrane to extract the proteolysed product and the buffer by removing the porous body and nanoparticles after the protease reaction. To conduct mass spectrometry on the peptide fragments of interest obtained by protease reaction, it is necessary to remove the porous body and nanoparticles.

The filtration membrane in a kit related to the present invention is preferred to be a type that functions as the "bottom of a reaction vessel" which hardly permeates the buffer and peptides produced by protease reaction under conditions that entail no pressure or centrifugation, while functioning as a "strainer" which allows permeation of the buffer and peptides during a centrifugation process or the like.

Centrifugal conditions are not limited particularly, but a range of 3,000~10,000 g is preferred for the buffer and peptides to pass through the filtration membrane.

As for a filtration membrane suitable for a kit related to the present invention, a filtration membrane made of polyvinylidene difluoride (PVDF) (low-binding hydrophilic PVDF, pore size of 0.2 Millipore), for example, may be used.

To simultaneously process multiple samples, available kits include a filtration membrane made of PVDF and housing material made of polyacrylonitrile resin, for example, Barex® (Mitsui Fine Chemicals, Inc.)

A kit related to the present invention may also include instructions for the kit and/or conditions for mass spectrometry for detection of monoclonal antibodies.

Moreover, a kit related to the present invention may include at least one internal standard peptide. By analyzing the internal standard peptide at the same time as or separately from the sample under the same conditions, even further accurate analysis results are achieved. The internal standard peptide contains the amino-acid sequence specific to a target monoclonal antibody and is the type that is produced through proteolysis by the protease included in the kit.

For example, when the detection target is trastuzumab, trastuzumab-DM1, bevacizumab or rituximab, one or more peptides may be selected from among those having amino-acid sequences with SEQ ID NO: 1~47 as the internal standard peptides.

More specifically, when the target monoclonal antibody is trastuzumab or trastuzumab-DM1, and when the protease is Trypsin Gold (Promega), one or more peptides may be selected from among those having amino-acid sequences of SEQ ID NO: 1~7 as the internal standard peptides.

When the target monoclonal antibody is bevacizumab, and when the protease is Trypsin Gold (Promega), one or more peptides may be selected from among those having amino-acid sequences with SEQ ID NO: 8~12 as the internal standard peptides.

When the target monoclonal antibody is rituximab, and when the protease is Trypsin Gold (Promega), one or more peptides may be selected from among those having amino-acid sequences with SEQ ID NO: 13~19 as the internal standard peptides.

When the target monoclonal antibody is trastuzumab or trastuzumab-DM1, and when the protease is Trypsin TPCK-treated (Sigma-Aldrich), one or more peptides may be selected from among those having amino-acid sequences with SEQ ID NO: 20~28, 46 and 47, in addition to those having amino-acid sequences of SEQ ID NO: 1~7, as the internal standard peptides.

When the target monoclonal antibody is bevacizumab, and when the protease is Trypsin TPCK-treated (Sigma-Aldrich), one or more peptides may be selected from among those having amino-acid sequences with SEQ ID NO: 29~38, in addition to those having amino-acid sequences of SEQ ID NO: 8~12, as the internal standard peptides.

When the target monoclonal antibody is rituximab, and when the protease is Trypsin TPCK-treated (Sigma-Aldrich), one or more peptides may be selected from among those having amino-acid sequences with SEQ ID NO: 39~45, in addition to those having amino-acid sequences of SEQ ID NO: 13~19, as the internal standard peptides.

As for internal standard peptides, it is preferred to be those having the amino-acid sequence specific to the target monoclonal, more particularly, the amino-acid sequence in the (Fab) domains; even more preferably, to be those having the amino-acid sequence including the amino acids derived from the CDR2 region of heavy or light chains.

Using a kit related to the present invention makes it further simplified, or even automated by a device, to prepare peptide fragments for identification/quantification of a monoclonal antibody of interest. Especially, since trypsin or the like maintains its activity even when immobilized on nanoparticle surfaces, preparation of peptide fragments is further simplified by the kit that provides a protease immobilized on nanoparticle surfaces.

A kit provided in the embodiments of the present invention is structured as follows, for example.

<1. For Analysis of Single Sample>

A reagent kit for analyzing one sample at a time is structured to have the following, for example.

- 0.2-μm membrane centrifugal filter (Millipore Ultrafree, PVDF, 0.2 μm)
- 100-nm protein G resin slurry (stored at 4° C.)
- trypsin and protease beads immobilized on 200-nm nanoparticles (stored at −20° C.)
- low adsorption plate for plasma dilution
- microtube for solution recovery
- buffer for plasma dilution (PBS+0.1% n-octyl-β-D-thioglycoside or corresponding surfactant, for example, n-octyl-β-D-glycoside)
- buffer for washing beads (PBS)
- buffer for protease reaction (25 mM Tris-HCl, pH 8.0+ protease reaction promoter)
- 10% formic-acid solution
- instructions <2. For Analysis of Multiple Samples>

A reagent kit for simultaneously analyzing multiple samples, for example 96 samples, is structured to have the following, for example.

0.2-μm filter membrane plate (Millipore MultiScreen PVDF, Barex, 0.2 μm)
100-nm protein G resin slurry (stored at 4° C.)
trypsin and protease beads immobilized on 200-nm nanoparticles (stored at −20° C.)
low adsorption plate for plasma dilution
plate for solution recovery
plate reservoir for solution disposal
plate for protease beads
buffer for plasma dilution (PBS+0.1% n-octyl-β-D-thioglycoside or corresponding surfactant, for example n-octyl-β-D-glycoside)
buffer for washing beads (PBS)
buffer for protease reaction (25 mM Tris-HCl, pH 8.0+ protease reaction promoter)
10% formic-acid solution
plate cover seal
DMSO resistant needle-pierceable plate cover seal
instructions <Additional Reagent>

Internal standard peptides, for example, are those to be included in a kit related to the present invention. Internal standard peptides are for enhancing accuracy when quantifying a biopharmaceutical peptide for quantitative analysis. It is preferred to prepare multiple peptides for each biopharmaceutical product, which are then offered for separate commercial distributions. Internal standard peptides may include those labeled with stable isotope amino acids. In such a case, since mass spectrometry quantification conditions differ from those without isotopes, it is preferred to enclose quantification conditions for internal standard peptides.

<Contents> internal standard peptide (at least one peptide with SEQ ID NO: 1~7 for trastuzumab, for example)
reagent quality warranty data (mass spectrometry data and atomic purity measurement results)
file package of quantification conditions
instructions <Method Package>

The present invention also provides a method package to be used for the monoclonal antibody detection method, which is conducted by bringing a porous body with a target monoclonal antibody immobilized in its pores and nanoparticles with immobilized trypsin into contact in a liquid so as to perform selective trypsin proteolysis of the monoclonal antibody and then by analyzing the obtained peptide fragments through high-performance liquid chromatography-mass spectrometry (LC-MS). In the present application, the "method package" means a package that includes computer readable LC-MS conditions for analyzing a specific detection target and is available for individual distributions. When imported in LC-MS, the data in the method package allows targets to be analyzed under optimal conditions that have been obtained after detailed studies.

As described above, detection by mass spectrometry allows significantly highly accurate analysis, but analysis conditions are totally different depending on the ions of interest. Thus, setting proper analysis conditions is important but difficult, and setting conditions is time-consuming. Accordingly, preparing conditions in advance provides users with enhanced convenience for their mass spectrometry. The applicant of the present invention has offered method packages for users to perform LC-MS analysis on pesticides and animal drugs, for example, by simplified methods. The present invention now provides another method package for identifying/quantifying a monoclonal antibody in a sample through LC-MS.

Namely, the present invention relates to a computer readable recording medium with loaded data for executing mass spectrometry in a method for detecting a monoclonal antibody; the method is conducted by bringing a porous body with a target monoclonal antibody immobilized in its pores and nanoparticles with an immobilized protease into contact with each other in a liquid so as to perform selective proteolysis of the monoclonal antibody, and then by analyzing the obtained peptide fragments through high-performance liquid chromatography-mass spectrometry (LC-MS). The medium include, but are not limited to, data on at least parent ions, fragment ions, expected retention time, and voltage at each quadrupole (Q1, Q2, Q3) of a triple-quadrupole mass spectrometer for at least one peptide obtained by protease reaction of the monoclonal antibody, for example, a peptide having the amino-acid sequence that includes the amino acids in the (Fab) domain, more preferably in the CDR regions. Since values in the data such as expected retention time and voltages vary depending on the device and detection conditions, it is preferred to provide values corresponding to the device to be used. For better performance by those skilled in the art, it is preferred to provide a range of values if the values are expected to vary under different conditions.

The recording medium is not limited particularly; examples are discs and memories capable of recording information magnetically or optically.

More specifically, the method package may include the following information and software functions.

optimized* m/z value of parent ions
optimized m/z value of fragment ions
optimized Q1 pre-bias voltage value
optimized Q2 collision energy voltage value
optimized Q3 pre-bias voltage value
expected retention time and mass spectrometry time of target ions
quantification conversion formula
function of outputting analysis results report

* Measure each condition topic, select the strongest ion intensity and most repeatable m/z value, and set it as the optimized value The present invention also provides a method package for a detection of a monoclonal antibody through high-performance liquid chromatography-mass spectrometry (LC-MS); the package includes the above recording medium and instructions for the recording medium.

Examples of recording media and method packages include those containing exclusive information on specific monoclonal antibodies. Therefore, if the monoclonal antibody is trastuzumab, trastuzumab-DM1, bevacizumab or rituximab, a recording medium or a method package is provided to contain analysis conditions suitable for each of such antibodies.

In the above examples, data loaded on the recording medium are for analysis conditions on peptides having at least one amino-acid sequence with SEQ ID NO: 1~47, for example.

Data loaded on a method package may be common data to be shared by multiple mass spectrometers, or various data applicable for analysis to be conducted by a specific mass spectrometer.

The recording medium and method package may be provided along with a kit related to the present invention or separately from the kit.

EXAMPLES

The present invention is described in further detail by referring to the following examples. However, the present invention is not limited to the examples below.

Example 1: Sample Preparation Kit

A kit structured as follows is prepared for analyzing a single sample.
(1) PBS buffer (PBS+0.1% n-octyl-β-D-thioglucoside, Dojindo)
(2) enzyme reaction buffer (25 mM Tris-HCl, pH 8.0)
(3) enzyme reaction termination solution (10% formic acid)
(4) filter tube (low-binding hydrophilic PVDF, pore size 0.2 μm, Millipore)
(5) low adsorption tube (Richell Microresico® tube 92017)
(6) LC-MS vial, insert (Shimadzu GLC, GLC4010-VP, Target vial VP, Target Polyspring insert C4010-630P)
(7) porous body (Pierce Protein G UltraLink Resin 53126, 40 μL dispense)
(8) nanoparticles (trypsin immobilized FG beads (trypsin 40 μg))
(9) instructions <Protocol (Stated on (9) Instructions)>
1. Take 20 μL of blood sample in low adsorption tube (5), and dilute it with 180 μL of buffer (1).
2. Centrifuge porous body (7) using a tabletop-type centrifugal device and discard the supernatant; add 100 μL of buffer (1), gently stir and centrifuge the mixture; discard the supernatant; repeat the process three times; then, add 40 μL of buffer (1) to form a suspension, which is transferred to filter tube (4); the process here may also be conducted in filter tube (4).
3. Transfer the diluted blood sample in step (1) to filter tube (4).
4. While lightly tapping using a tapping rotary mixer (Nissin Rika), stir the sample at room temperature for 1 hour.
5. Perform centrifugal filtration (10,000 g×1 min) to separate the solution; add 200 μL of buffer (1) and perform centrifugal filtration; discard the filtrate; repeat the process three times.
6. Add 200 μL of PBS buffer (1) and gently stir the mixture; perform centrifugal filtration and discard the filtrate; the process is performed only once.
7. Add 200 μL of buffer (2) to the porous body in step (6).
8. Dissolve nanoparticles (8) on ice, and homogeneously disperse quickly in an ultrasonic cleaner or a vortex mixer; add the mixture to step 7.
9. Attach the solution-recovery tube to the filter tube, and seal the lid side with a Parafilm or the like; perform proteolysis by stirring the tube for 6 hours at 37° C., while gently tapping with a tapping rotary mixer.
10. Perform centrifugal filtration (10,000 g×1 min.) on the reaction mixture to remove the resin; collect the filtrate.
11. Add 15 μL of enzyme reaction termination solution (3) to step (10).
12. Transfer to LC-MS vial set (6) and remove air bubbles at the bottom.
13. Set the sample onto the LC-MS autosampler for analysis.
14. Conditions list for LC-MS analysis is provided on the appendix (Table 1 to Table 6).

<Conditions for Peptide Mass Spectrometry for Therapeutic Antibody Quantification (Loaded on Recording Medium)>

TABLE 1

Peptides for Quantification of Trastuzumab and Trastuzumab-DM1 along with Data for Mass Spectrometry
Solid-phase enzyme: Trypsin Gold (Promega)

| Peptide Sequence | Parent Ion m/z | Fragment Ion m/z | Retention Time [min] | Q1 Pre Bias [V] | Collision Energy [V] | Q3 Pre Bias [V] |
|---|---|---|---|---|---|---|
| IYPTNGYTR | 542.8 | 808.4 | 3.405 | −40 | −18 | −30 |
| IYPTNGYTR | 542.8 | 711.3 | 3.405 | −40 | −26 | −38 |
| IYPTNGYTR | 542.8 | 610.3 | 3.405 | −40 | −24 | −22 |
| IYPTNGYTR | 542.8 | 404.7 | 3.405 | −20 | −18 | −15 |
| IYPTNGYTR | 542.8 | 277.2 | 3.405 | −20 | −16 | −30 |
| AEDTAVYYCSR | 667.8 | 1134.5 | 3.473 | −24 | −24 | −34 |
| AEDTAVYYCSR | 667.8 | 1019.5 | 3.473 | −24 | −25 | −30 |
| AEDTAVYYCSR | 667.8 | 918.4 | 3.473 | −24 | −25 | −36 |
| AEDTAVYYCSR | 667.8 | 847.4 | 3.473 | −24 | −23 | −32 |
| AEDTAVYYCSR | 667.8 | 748.3 | 3.473 | −24 | −21 | −40 |
| AEDTAVYYCSR | 667.8 | 585.2 | 3.473 | −24 | −24 | −22 |
| AEDTAVYYCSR | 667.8 | 422.2 | 3.473 | −24 | −22 | −30 |
| AEDTAVYYCSR | 667.8 | 488.2 | 3.473 | −24 | −20 | −25 |
| FTISADTSK | 485.2 | 822.4 | 3.635 | −18 | −18 | −32 |
| FTISADTSK | 485.2 | 721.4 | 3.635 | −11 | −18 | −26 |

TABLE 1-continued

Peptides for Quantification of Trastuzumab and Trastuzumab-DM1 along with Data for Mass Spectrometry
Solid-phase enzyme: Trypsin Gold (Promega)

| Peptide Sequence | Parent Ion m/z | Fragment Ion m/z | Retention Time [min] | Q1 Pre Bias [V] | Collision Energy [V] | Q3 Pre Bias [V] |
|---|---|---|---|---|---|---|
| FTISADTSK | 485.2 | 608.3 | 3.635 | -18 | -19 | -32 |
| FTISADTSK | 485.2 | 521.3 | 3.635 | -18 | -19 | -38 |
| FTISADTSK | 485.2 | 335.2 | 3.635 | -18 | -24 | -24 |
| LSCAASGFNIK | 584.3 | 967.5 | 3.921 | -40 | -21 | -36 |
| LSCAASGFNIK | 584.3 | 807.4 | 3.921 | -40 | -22 | -30 |
| LSCAASGFNIK | 584.3 | 736.4 | 3.921 | -40 | -22 | -38 |
| LSCAASGFNIK | 584.3 | 665.4 | 3.921 | -40 | -21 | -34 |
| LSCAASGFNIK | 584.3 | 578.3 | 3.921 | -22 | -23 | -40 |
| LSCAASGFNIK | 584.3 | 484.2 | 3.921 | -40 | -19 | -17 |
| DTYIHWVR | 363.9 | 597.3 | 4.097 | -27 | -17 | -22 |
| DTYIHWVR | 363.9 | 460.3 | 4.097 | -27 | -19 | -23 |
| DTYIHWVR | 363.9 | 437.2 | 4.097 | -27 | -11 | -30 |
| DTYIHWVR | 363.9 | 299.2 | 4.097 | -26 | -16 | -21 |
| GLEWVAR | 415.7 | 660.3 | 4.077 | -30 | -15 | -24 |
| GLEWVAR | 415.7 | 531.3 | 4.077 | -30 | -16 | -40 |
| GLEWVAR | 415.7 | 345.2 | 4.077 | -16 | -17 | -24 |
| GLEWVAR | 415.7 | 246.2 | 4.077 | -30 | -18 | -17 |
| NTAYLQMNSLR | 655.8 | 1095.6 | 4.144 | -24 | -23 | -42 |
| NTAYLQMNSLR | 655.8 | 1024.5 | 4.144 | -24 | -22 | -40 |
| NTAYLQMNSLR | 655.8 | 861.5 | 4.144 | -24 | -22 | -32 |
| NTAYLQMNSLR | 655.8 | 748.4 | 4.144 | -24 | -23 | -28 |
| NTAYLQMNSLR | 655.8 | 620.3 | 4.144 | -24 | -23 | -32 |
| NTAYLQMNSLR | 655.8 | 489.3 | 4.144 | -24 | -23 | -25 |
| NTAYLQMNSLR | 655.8 | 375.2 | 4.144 | -24 | -22 | -19 |

*Peptide containing "C" is processed with reductive alkylation.

TABLE 2

Peptides for Quantification of Bevacizumab along with Data for Mass Spectrometry
Solid-phase enzyme: Trypsin Gold (Promega)

| Peptide Sequence | Parent Ion m/z | Fragment Ion m/z | Retention Time [min] | Q1 Pre Bias [V] | Collision Energy [V] | Q3 Pre Bias [V] |
|---|---|---|---|---|---|---|
| AEDTAVYYCAK | 645.8 | 1090.5 | 3.501 | -24 | -22 | -42 |
| AEDTAVYYCAK | 645.8 | 975.5 | 3.501 | -24 | -24 | -38 |
| AEDTAVYYCAK | 645.8 | 874.4 | 3.501 | -24 | -23 | -34 |
| AEDTAVYYCAK | 645.8 | 803.4 | 3.501 | -24 | -20 | -30 |
| AEDTAVYYCAK | 645.8 | 704.3 | 3.501 | -24 | -20 | -38 |

TABLE 2-continued

Peptides for Quantification of Bevacizumab along with Data for Mass Spectrometry
Solid-phase enzyme: Trypsin Gold (Promega)

| Peptide Sequence | Parent Ion m/z | Fragment Ion m/z | Retention Time [min] | Q1 Pre Bias [V] | Collision Energy [V] | Q3 Pre Bias [V] |
|---|---|---|---|---|---|---|
| AEDTAVYYCAK | 645.8 | 541.2 | 3.501 | -24 | -21 | -40 |
| AEDTAVYYCAK | 645.8 | 488.2 | 3.501 | -24 | -17 | -11 |
| AEDTAVYYCAK | 645.8 | 587.3 | 3.501 | -24 | -17 | -22 |
| STAYLQMNSLR | 642.3 | 1095.6 | 4.147 | -24 | -24 | -42 |
| STAYLQMNSLR | 642.3 | 1024.5 | 4.147 | -24 | -25 | -40 |
| STAYLQMNSLR | 642.3 | 861.5 | 4.147 | -24 | -25 | -20 |
| STAYLQMNSLR | 642.3 | 748.4 | 4.147 | -24 | -22 | -28 |
| STAYLQMNSLR | 642.3 | 620.3 | 4.147 | -24 | -24 | -32 |
| STAYLQMNSLR | 642.3 | 489.3 | 4.147 | -24 | -22 | -25 |
| STAYLQMNSLR | 642.3 | 375.2 | 4.147 | -24 | -22 | -27 |
| FTFSLDTSK | 523.3 | 898.5 | 4.432 | -38 | -20 | -34 |
| FTFSLDTSK | 523.3 | 797.4 | 4.432 | -38 | -18 | -30 |
| FTFSLDTSK | 523.3 | 650.3 | 4.432 | -38 | -19 | -34 |
| FTFSLDTSK | 523.3 | 563.3 | 4.432 | -38 | -22 | -40 |
| FTFSLDTSK | 523.3 | 450.2 | 4.432 | -20 | -23 | -30 |
| FTFSLDTSK | 523.3 | 335.2 | 4.432 | -20 | -25 | -24 |
| FTFSLDTSK | 523.3 | 399.2 | 4.432 | -38 | -17 | -11 |
| FTFSLDTSK | 523.3 | 249.1 | 4.432 | -38 | -17 | -17 |
| VLIYFTSSLHSGVPSR | 588.3 | 832.4 | 4.515 | -22 | -19 | -30 |
| VLIYFTSSLHSGVPSR | 588.3 | 775.9 | 4.515 | -22 | -18 | -28 |
| VLIYFTSSLHSGVPSR | 588.3 | 719.4 | 4.515 | -22 | -18 | -26 |
| VLIYFTSSLHSGVPSR | 588.3 | 637.8 | 4.515 | -22 | -18 | -24 |
| VLIYFTSSLHSGVPSR | 588.3 | 564.3 | 4.515 | -22 | -22 | -20 |
| VLIYFTSSLHSGVPSR | 588.3 | 602.3 | 4.515 | -22 | -28 | -22 |
| VLIYFTSSLHSGVPSR | 588.3 | 359.2 | 4.515 | -22 | -26 | -26 |
| VLIYFTSSLHSGVPSR | 588.3 | 213.2 | 4.515 | -22 | -20 | -23 |
| LSCAASGYTFTNYGMNWVR | 733.3 | 1039.5 | 4.896 | -28 | -25 | -40 |
| LSCAASGYTFTNYGMNWVR | 733.3 | 848.4 | 4.896 | -28 | -18 | -32 |
| LSCAASGYTFTNYGMNWVR | 733.3 | 925.4 | 4.896 | -28 | -25 | -36 |
| LSCAASGYTFTNYGMNWVR | 733.3 | 762.4 | 4.896 | -28 | -26 | -40 |
| LSCAASGYTFTNYGMNWVR | 733.3 | 705.4 | 4.896 | -26 | -24 | -34 |
| LSCAASGYTFTNYGMNWVR | 733.3 | 574.3 | 4.896 | -28 | -22 | -30 |
| LSCAASGYTFTNYGMNWVR | 733.3 | 520.2 | 4.896 | -28 | -18 | -36 |
| LSCAASGYTFTNYGMNWVR | 733.3 | 503.2 | 4.896 | -28 | -18 | -36 |

*Peptide containing "C" is processed with reductive alkylation.

TABLE 3

Peptides for Quantification of Rituximab along with Data for Mass Spectrometry
Solid-phase enzyme: Trypsin Gold (Promega)

| Peptide Sequence | Parent Ion m/z | Fragment Ion m/z | Retention Time [min] | Q1 Pre Bias [V] | Collision Energy [V] | Q3 Pre Bias [V] |
|---|---|---|---|---|---|---|
| ATLTADK | 360.2 | 648.4 | 2.809 | -26 | -14 | -24 |
| ATLTADK | 360.2 | 547.3 | 2.81 | -13 | -13 | -20 |
| ATLTADK | 360.2 | 434.2 | 2.81 | -26 | -16 | -22 |
| ATLTADK | 360.2 | 333.2 | 2.81 | -26 | -19 | -24 |
| ATLTADK | 360.2 | 262.1 | 2.81 | -13 | -21 | -29 |
| VTMTCR | 384.2 | 668.3 | 2.887 | -28 | -16 | -34 |
| VTMTCR | 384.2 | 567.2 | 2.887 | -28 | -14 | -40 |
| VTMTCR | 384.2 | 436.2 | 2.887 | -28 | -16 | -16 |
| VTMTCR | 384.2 | 335.1 | 2.887 | -14 | -17 | -23 |
| VTMTCR | 384.2 | 201.1 | 2.887 | -28 | -14 | -21 |
| LASGVPVR | 399.7 | 685.4 | 3.426 | -29 | -17 | -34 |
| LASGVPVR | 399.7 | 614.4 | 3.426 | -30 | -16 | -32 |
| LASGVPVR | 399.7 | 527.3 | 3.426 | -15 | -16 | -38 |
| LASGVPVR | 399.7 | 371.2 | 3.426 | -15 | -17 | -28 |
| ATSNLASGVPVR | 586.3 | 912.5 | 3.728 | -22 | -25 | -34 |
| ATSNLASGVPVR | 586.3 | 685.4 | 3.728 | -22 | -23 | -38 |
| ATSNLASGVPVR | 586.3 | 614.4 | 3.728 | -22 | -25 | -24 |
| ATSNLASGVPVR | 586.3 | 527.3 | 3.728 | -22 | -25 | -40 |
| ATSNLASGVPVR | 586.3 | 470.3 | 3.728 | -22 | -19 | -17 |
| ATSNLASGVPVR | 586.3 | 371.2 | 3.728 | -22 | -17 | -27 |
| FSGSGSGTSYSLTISR | 803.9 | 1084.6 | 4.051 | -30 | -32 | -42 |
| FSGSGSGTSYSLTISR | 803.9 | 926.5 | 4.051 | -30 | -34 | -36 |
| FSGSGSGTSYSLTISR | 803.9 | 839.5 | 4.051 | -30 | -36 | -32 |
| FSGSGSGTSYSLTISR | 803.9 | 839.5 | 4.051 | -30 | -36 | -32 |
| FSGSGSGTSYSLTISR | 803.9 | 589.4 | 4.051 | -30 | -34 | -22 |
| FSGSGSGTSYSLTISR | 803.9 | 476.3 | 4.051 | -30 | -32 | -17 |
| FSGSGSGTSYSLTISR | 803.9 | 375.2 | 4.051 | -30 | -33 | -27 |
| ASGYTFTSYNMHWVK | 597.9 | 1064.5 | 4.399 | -22 | -24 | -40 |
| ASGYTFTSYNMHWVK | 597.9 | 860.9 | 4.399 | -22 | -18 | -32 |
| ASGYTFTSYNMHWVK | 597.9 | 817.4 | 4.399 | -22 | -18 | -30 |
| ASGYTFTSYNMHWVK | 597.9 | 788.9 | 4.399 | -22 | -18 | -30 |
| ASGYTFTSYNMHWVK | 597.9 | 707.3 | 4.399 | -22 | -18 | -26 |
| ASGYTFTSYNMHWVK | 597.9 | 656.8 | 4.399 | -22 | -18 | -24 |
| ASGYTFTSYNMHWVK | 597.9 | 583.3 | 4.399 | -22 | -22 | -22 |
| ASSSVSYIHWFQQK | 556.6 | 798.9 | 4.399 | -20 | -17 | -30 |
| ASSSVSYIHWFQQK | 556.6 | 755.4 | 4.399 | -20 | -16 | -28 |
| ASSSVSYIHWFQQK | 556.6 | 711.9 | 4.399 | -20 | -19 | -26 |

TABLE 3-continued

Peptides for Quantification of Rituximab along with Data for Mass Spectrometry
Solid-phase enzyme: Trypsin Gold (Promega)

| Peptide Sequence | Parent Ion m/z | Fragment Ion m/z | Retention Time [min] | Q1 Pre Bias [V] | Collision Energy [V] | Q3 Pre Bias [V] |
|---|---|---|---|---|---|---|
| ASSSVSYIHWFQQK | 556.6 | 668.3 | 4.399 | -40 | -16 | -24 |
| ASSSVSYIHWFQQK | 556.6 | 618.8 | 4.399 | -20 | -17 | -22 |
| ASSSVSYIHWFQQK | 556.6 | 550.3 | 4.399 | -20 | -14 | -40 |
| ASSSVSYIHWFQQK | 556.6 | 403.2 | 4.399 | -20 | -29 | -25 |

*Peptide containing "C" is processed with reductive alkylation.

TABLE 4

Peptides for Quantification of Trastuzumab and Trastuzumab-DM1 along with Data for Mass Spectrometry
Solid-phase enzyme: Trypsin TPCK-treated (Sigma-Aldrich)

| Peptide Sequence | Parent Ion m/z | Fragment Ion m/z | Retention Time [min] | Q1 Pre Bias [V] | Collision Energy [V] | Q3 Pre Bias [V] |
|---|---|---|---|---|---|---|
| VTITCR | 375.2 | 650.3 | 3.077 | -30 | -16 | -34 |
| VTITCR | 375.2 | 549.3 | 3.077 | -28 | -14 | -40 |
| VTITCR | 375.2 | 436.2 | 3.077 | -14 | -16 | -16 |
| VTITCR | 375.2 | 201.1 | 3.077 | -28 | -13 | -22 |
| LYSGVPSR | 439.7 | 765.4 | 3.343 | -30 | -19 | -28 |
| LYSGVPSR | 439.7 | 602.3 | 3.343 | -10 | -17 | -22 |
| LYSGVPSR | 439.7 | 515.3 | 3.343 | -16 | -18 | -38 |
| LYSGVPSR | 439.7 | 359.2 | 3.343 | -30 | -16 | -25 |
| LYSGVPSR | 439.7 | 277.2 | 3.343 | -30 | -15 | -10 |
| IHWVR | 355.7 | 597.3 | 3.253 | -13 | -16 | -22 |
| IHWVR | 355.7 | 460.3 | 3.253 | -13 | -16 | -17 |
| IHWVR | 355.7 | 299.2 | 3.253 | -26 | -16 | -20 |
| IHWVR | 355.7 | 251.2 | 3.253 | -26 | -15 | -28 |
| TTPPTFGQGTK | 567.8 | 932.5 | 3.401 | -40 | -19 | -36 |
| TTPPTFGQGTK | 567.8 | 835.4 | 3.401 | -40 | -25 | -32 |
| TTPPTFGQGTK | 567.8 | 466.8 | 3.401 | -40 | -19 | -17 |
| TTPPTFGQGTK | 567.8 | 418.2 | 3.401 | -22 | -26 | -30 |
| AEDTAVY | 768.3 | 316.1 | 3.439 | -28 | -34 | -22 |
| AEDTAVY | 768.3 | 488.2 | 3.439 | -28 | -25 | -18 |
| AEDTAVY | 768.3 | 587.3 | 3.439 | -28 | -23 | -30 |
| IYPTNGYTR | 542.8 | 808.4 | 3.364 | -40 | -18 | -30 |
| IYPTNGYTR | 542.8 | 711.3 | 3.364 | -40 | -26 | -38 |
| IYPTNGYTR | 542.8 | 404.7 | 3.364 | -20 | -18 | -15 |
| IYPTNGYTR | 542.8 | 277.2 | 3.364 | -20 | -16 | -30 |
| IYPTNGYTR | 542.8 | 808.4 | 3.364 | -40 | -18 | -30 |

TABLE 4-continued

Peptides for Quantification of Trastuzumab and Trastuzumab-DM1 along with Data for Mass Spectrometry
Solid-phase enzyme: Trypsin TPCK-treated (Sigma-Aldrich)

| Peptide Sequence | Parent Ion m/z | Fragment Ion m/z | Retention Time [min] | Q1 Pre Bias [V] | Collision Energy [V] | Q3 Pre Bias [V] |
|---|---|---|---|---|---|---|
| AEDTAVYYCSR | 667.8 | 1134.5 | 3.434 | −24 | −24 | −34 |
| AEDTAVYYCSR | 667.8 | 1019.5 | 3.434 | −24 | −25 | −30 |
| AEDTAVYYCSR | 667.8 | 918.4 | 3.434 | −24 | −25 | −36 |
| AEDTAVYYCSR | 667.8 | 847.4 | 3.434 | −24 | −23 | −32 |
| AEDTAVYYCSR | 667.8 | 748.3 | 3.434 | −24 | −21 | −40 |
| AEDTAVYYCSR | 667.8 | 585.2 | 3.434 | −24 | −24 | −22 |
| AEDTAVYYCSR | 667.8 | 422.2 | 3.434 | −24 | −22 | −30 |
| AEDTAVYYCSR | 667.8 | 488.2 | 3.434 | −24 | −20 | −25 |
| LQMNSLR | 431.2 | 748.4 | 3.572 | −16 | −20 | −28 |
| LQMNSLR | 431.2 | 620.3 | 3.572 | −16 | −18 | −32 |
| LQMNSLR | 431.2 | 489.3 | 3.572 | −16 | −19 | −18 |
| LQMNSLR | 431.2 | 242.1 | 3.572 | −16 | −16 | −27 |
| FTISADTSK | 485.2 | 822.4 | 3.599 | −18 | −18 | −32 |
| FTISADTSK | 485.2 | 721.4 | 3.599 | −11 | −18 | −26 |
| FTISADTSK | 485.2 | 608.3 | 3.599 | −18 | −19 | −32 |
| FTISADTSK | 485.2 | 521.3 | 3.599 | −18 | −19 | −38 |
| FTISADTSK | 485.2 | 335.2 | 3.599 | −18 | −24 | −24 |
| LSCAASGFNIK | 584.3 | 967.5 | 3.865 | −40 | −21 | −36 |
| LSCAASGFNIK | 584.3 | 807.4 | 3.865 | −40 | −22 | −30 |
| LSCAASGFNIK | 584.3 | 736.4 | 3.865 | −40 | −22 | −38 |
| LSCAASGFNIK | 584.3 | 665.4 | 3.865 | −40 | −21 | −34 |
| LSCAASGFNIK | 584.3 | 578.3 | 3.865 | −22 | −23 | −40 |
| LSCAASGFNIK | 584.3 | 484.2 | 3.865 | −40 | −19 | −17 |
| DTYIHWVR | 363.9 | 597.3 | 4.056 | −27 | −17 | −22 |
| DTYIHWVR | 363.9 | 460.3 | 4.056 | −27 | −19 | −23 |
| DTYIHWVR | 363.9 | 437.2 | 4.056 | −27 | −11 | −30 |
| DTYIHWVR | 363.9 | 299.2 | 4.056 | −26 | −16 | −21 |
| GLEWVAR | 415.7 | 660.3 | 4.033 | −30 | −15 | −24 |
| GLEWVAR | 415.7 | 531.3 | 4.033 | −30 | −16 | −40 |
| GLEWVAR | 415.7 | 345.2 | 4.033 | −16 | −17 | −24 |
| GLEWVAR | 415.7 | 246.2 | 4.033 | −30 | −18 | −17 |
| NTAYLQMNSLR | 655.8 | 1095.6 | 4.099 | −24 | −23 | −42 |
| NTAYLQMNSLR | 655.8 | 1024.5 | 4.099 | −24 | −22 | −40 |
| NTAYLQMNSLR | 655.8 | 861.5 | 4.099 | −24 | −22 | −32 |
| NTAYLQMNSLR | 655.8 | 748.4 | 4.099 | −24 | −23 | −28 |
| NTAYLQMNSLR | 655.8 | 620.3 | 4.099 | −24 | −23 | −32 |

TABLE 4-continued

Peptides for Quantification of Trastuzumab and Trastuzumab-DM1 along with Data for Mass Spectrometry
Solid-phase enzyme: Trypsin TPCK-treated (Sigma-Aldrich)

| Peptide Sequence | Parent Ion m/z | Fragment Ion m/z | Retention Time [min] | Q1 Pre Bias [V] | Collision Energy [V] | Q3 Pre Bias [V] |
|---|---|---|---|---|---|---|
| NTAYLQMNSLR | 655.8 | 489.3 | 4.099 | -24 | -23 | -25 |
| NTAYLQMNSLR | 655.8 | 375.2 | 4.099 | -24 | -22 | -19 |
| DTYIHW | 417.7 | 719.4 | 4.425 | -16 | -16 | -26 |
| DTYIHW | 417.7 | 618.3 | 4.425 | -16 | -13 | -22 |
| DTYIHW | 417.7 | 455.2 | 4.425 | -30 | -14 | -17 |
| DTYIHW | 417.7 | 342.2 | 4.425 | -30 | -19 | -24 |
| WGGDGFY | 801.3 | 416.2 | 4.499 | -30 | -30 | -15 |
| WGGDGFY | 801.3 | 473.2 | 4.499 | -30 | -30 | -23 |
| WGGDGFY | 801.3 | 620.2 | 4.499 | -30 | -26 | -32 |
| WGGDGFY | 801.3 | 602.2 | 4.499 | -30 | -30 | -22 |
| LLIYSASF | 913.5 | 687.3 | 5.149 | -36 | -31 | -26 |
| LLIYSASF | 913.5 | 574.3 | 5.149 | -34 | -31 | -40 |
| LLIYSASF | 913.5 | 503.3 | 5.149 | -22 | -30 | -36 |
| LLIYSASF | 913.5 | 590.4 | 5.149 | -36 | -29 | -30 |
| LLIYSASF | 913.5 | 661.4 | 5.149 | -38 | -27 | -34 |
| LLIYSASF | 913.5 | 748.4 | 5.149 | -36 | -26 | -28 |
| LLIYSASF | 913.5 | 643.4 | 5.149 | -34 | -30 | -24 |

*Peptide containing "C" is processed with reductive alkylation.

TABLE 5

Peptides for Quantification of Bevacizumab along with Data for Mass Spectrometry
Solid-phase enzyme: Trypsin TPCK-treated (Sigma-Aldrich)

| Peptide Sequence | Parent Ion m/z | Fragment Ion m/z | Retention Time [min] | Q1 Pre Bias [V] | Collision Energy [V] | Q3 Pre Bias [V] |
|---|---|---|---|---|---|---|
| TSSLHSGVPSR | 564.3 | 739.4 | 2.944 | -40 | -25 | -28 |
| TSSLHSGVPSR | 564.3 | 602.3 | 2.944 | -40 | -26 | -22 |
| TSSLHSGVPSR | 564.3 | 515.3 | 2.944 | -40 | -26 | -38 |
| TSSLHSGVPSR | 564.3 | 359.2 | 2.944 | -40 | -23 | -25 |
| FTSSLHSGVPSR | 425.6 | 564.3 | 3.326 | -16 | -15 | -40 |
| FTSSLHSGVPSR | 425.6 | 513.8 | 3.326 | -16 | -14 | -36 |
| FTSSLHSGVPSR | 425.6 | 470.3 | 3.326 | -16 | -17 | -17 |
| FTSSLHSGVPSR | 425.6 | 852.5 | 3.326 | -16 | -18 | -26 |
| FTSSLHSGVPSR | 425.6 | 739.4 | 3.326 | -30 | -21 | -28 |
| FTSSLHSGVPSR | 425.6 | 602.3 | 3.326 | -30 | -20 | -30 |
| FTSSLHSGVPSR | 425.6 | 515.3 | 3.326 | -16 | -21 | -38 |
| TGEPTYAADFKR | 452.6 | 534.8 | 3.495 | -17 | -15 | -40 |
| TGEPTYAADFKR | 452.6 | 599.3 | 3.495 | -17 | -15 | -22 |

TABLE 5-continued

Peptides for Quantification of Bevacizumab along with Data for Mass Spectrometry
Solid-phase enzyme: Trypsin TPCK-treated (Sigma-Aldrich)

| Peptide Sequence | Parent Ion m/z | Fragment Ion m/z | Retention Time [min] | Q1 Pre Bias [V] | Collision Energy [V] | Q3 Pre Bias [V] |
|---|---|---|---|---|---|---|
| TGEPTYAADFKR | 452.6 | 627.8 | 3.495 | -17 | -14 | -22 |
| TGEPTYAADFKR | 452.6 | 486.3 | 3.495 | -17 | -18 | -25 |
| TGEPTYAADFKR | 452.6 | 870.4 | 3.495 | -17 | -20 | -34 |
| TGEPTYAADFKR | 452.6 | 707.4 | 3.495 | -17 | -20 | -36 |
| AEDTAVYYCAK | 645.8 | 1090.5 | 3.476 | -24 | -22 | -42 |
| AEDTAVYYCAK | 645.8 | 975.5 | 3.476 | -24 | -24 | -38 |
| AEDTAVYYCAK | 645.8 | 874.4 | 3.476 | -24 | -23 | -34 |
| AEDTAVYYCAK | 645.8 | 803.4 | 3.476 | -24 | -20 | -30 |
| AEDTAVYYCAK | 645.8 | 704.3 | 3.476 | -24 | -20 | -38 |
| AEDTAVYYCAK | 645.8 | 541.2 | 3.476 | -24 | -21 | -40 |
| AEDTAVYYCAK | 645.8 | 488.2 | 3.476 | -24 | -17 | -11 |
| AEDTAVYYCAK | 645.8 | 587.3 | 3.476 | -24 | -17 | -22 |
| GMNWVR | 381.7 | 574.3 | 3.669 | -14 | -14 | -40 |
| GMNWVR | 381.7 | 460.3 | 3.669 | -30 | -15 | -17 |
| GMNWVR | 381.7 | 274.2 | 3.669 | -28 | -18 | -29 |
| INTYTGEPTYAADFKR | 616.3 | 867.4 | 3.858 | -24 | -18 | -32 |
| INTYTGEPTYAADFKR | 616.3 | 810.4 | 3.858 | -24 | -19 | -30 |
| INTYTGEPTYAADFKR | 616.3 | 759.9 | 3.858 | -24 | -20 | -28 |
| INTYTGEPTYAADFKR | 616.3 | 678.3 | 3.858 | -24 | -18 | -34 |
| INTYTGEPTYAADFKR | 616.3 | 627.8 | 3.858 | -24 | -18 | -32 |
| INTYTGEPTYAADFKR | 616.3 | 534.8 | 3.858 | -24 | -21 | -20 |
| INTYTGEPTYAADFKR | 616.3 | 1068.5 | 3.858 | -24 | -27 | -42 |
| INTYTGEPTYAADFKR | 616.3 | 707.4 | 3.858 | -24 | -27 | -36 |
| VTITCSASQDISNY | 779.9 | 984.4 | 4.212 | -30 | -21 | -38 |
| VTITCSASQDISNY | 779.9 | 826.4 | 4.212 | -30 | -19 | -32 |
| VTITCSASQDISNY | 779.9 | 739.3 | 4.212 | -30 | -20 | -40 |
| VTITCSASQDISNY | 779.9 | 611.3 | 4.212 | -30 | -18 | -22 |
| VTITCSASQDISNY | 779.9 | 496.2 | 4.212 | -30 | -20 | -17 |
| VTITCSASQDISNY | 779.9 | 948.4 | 4.212 | -30 | -18 | -36 |
| VTITCSASQDISNY | 779.9 | 1063.5 | 4.212 | -30 | -27 | -42 |
| VTITCSASQDISNY | 779.9 | 1176.6 | 4.212 | -30 | -19 | -46 |
| STAYLQMNSLR | 642.3 | 1095.6 | 4.105 | -24 | -24 | -42 |
| STAYLQMNSLR | 642.3 | 1024.5 | 4.105 | -24 | -25 | -40 |
| STAYLQMNSLR | 642.3 | 861.5 | 4.105 | -24 | -25 | -20 |
| STAYLQMNSLR | 642.3 | 748.4 | 4.105 | -24 | -22 | -28 |
| STAYLQMNSLR | 642.3 | 620.3 | 4.105 | -24 | -24 | -32 |

TABLE 5-continued

Peptides for Quantification of Bevacizumab along with Data for Mass Spectrometry
Solid-phase enzyme: Trypsin TPCK-treated (Sigma-Aldrich)

| Peptide Sequence | Parent Ion m/z | Fragment Ion m/z | Retention Time [min] | Q1 Pre Bias [V] | Collision Energy [V] | Q3 Pre Bias [V] |
|---|---|---|---|---|---|---|
| STAYLQMNSLR | 642.3 | 489.3 | 4.105 | -24 | -22 | -25 |
| STAYLQMNSLR | 642.3 | 375.2 | 4.105 | -24 | -22 | -27 |
| VLIYFTSSLH | 590.3 | 1080.6 | 4.791 | -22 | -20 | -44 |
| VLIYFTSSLH | 590.3 | 967.5 | 4.791 | -22 | -19 | -36 |
| VLIYFTSSLH | 590.3 | 854.4 | 4.791 | -22 | -20 | -32 |
| VLIYFTSSLH | 590.3 | 691.3 | 4.791 | -22 | -21 | -26 |
| VLIYFTSSLH | 590.3 | 544.3 | 4.791 | -22 | -23 | -28 |
| VLIYFTSSLH | 590.3 | 443.2 | 4.791 | -22 | -20 | -16 |
| VLIYFTSSLHSGVPSR | 588.3 | 832.4 | 4.476 | -22 | -19 | -30 |
| VLIYFTSSLHSGVPSR | 588.3 | 775.9 | 4.476 | -22 | -18 | -28 |
| VLIYFTSSLHSGVPSR | 588.3 | 719.4 | 4.476 | -22 | -18 | -26 |
| VLIYFTSSLHSGVPSR | 588.3 | 637.8 | 4.476 | -22 | -18 | -24 |
| VLIYFTSSLHSGVPSR | 588.3 | 564.3 | 4.476 | -22 | -22 | -20 |
| VLIYFTSSLHSGVPSR | 588.3 | 602.3 | 4.476 | -22 | -28 | -22 |
| VLIYFTSSLHSGVPSR | 588.3 | 359.2 | 4.476 | -22 | -26 | -26 |
| VLIYFTSSLHSGVPSR | 588.3 | 213.2 | 4.476 | -22 | -20 | -23 |
| FTFSLDTSK | 523.3 | 898.5 | 4.406 | -38 | -20 | -34 |
| FTFSLDTSK | 523.3 | 797.4 | 4.406 | -38 | -18 | -30 |
| FTFSLDTSK | 523.3 | 650.3 | 4.406 | -38 | -19 | -34 |
| FTFSLDTSK | 523.3 | 563.3 | 4.406 | -38 | -22 | -40 |
| FTFSLDTSK | 523.3 | 450.2 | 4.406 | -20 | -23 | -30 |
| FTFSLDTSK | 523.3 | 335.2 | 4.406 | -20 | -25 | -24 |
| FTFSLDTSK | 523.3 | 399.2 | 4.406 | -38 | -17 | -11 |
| FTFSLDTSK | 523.3 | 249.1 | 4.406 | -38 | -17 | -17 |
| VTITCSASQDISNYLNWYQQKPGK | 934.5 | 1244.6 | 4.875 | -40 | -28 | -48 |
| VTITCSASQDISNYLNWYQQKPGK | 934.5 | 1194.1 | 4.875 | -38 | -29 | -46 |
| VTITCSASQDISNYLNWYQQKPGK | 934.5 | 1114 | 4.875 | -40 | -28 | -42 |
| VTITCSASQDISNYLNWYQQKPGK | 934.5 | 1070.5 | 4.875 | -40 | -30 | -40 |
| VTITCSASQDISNYLNWYQQKPGK | 934.5 | 1035 | 4.875 | -40 | -28 | -40 |
| LSCAASGYTFTNYGMNWVR | 733.3 | 848.4 | 4.87 | -28 | -18 | -32 |
| LSCAASGYTFTNYGMNWVR | 733.3 | 1039.5 | 4.87 | -28 | -25 | -40 |
| LSCAASGYTFTNYGMNWVR | 733.3 | 925.4 | 4.87 | -28 | -25 | -36 |
| LSCAASGYTFTNYGMNWVR | 733.3 | 762.4 | 4.87 | -28 | -26 | -40 |
| LSCAASGYTFTNYGMNWVR | 733.3 | 705.4 | 4.87 | -26 | -24 | -34 |
| LSCAASGYTFTNYGMNWVR | 733.3 | 574.3 | 4.87 | -28 | -22 | -30 |
| LSCAASGYTFTNYGMNWVR | 733.3 | 520.2 | 4.87 | -28 | -18 | -36 |
| LSCAASGYTFTNYGMNWVR | 733.3 | 503.2 | 4.87 | -28 | -18 | -36 |

TABLE 5-continued

Peptides for Quantification of Bevacizumab along with Data for Mass Spectrometry
Solid-phase enzyme: Trypsin TPCK-treated (Sigma-Aldrich)

| Peptide Sequence | Parent Ion m/z | Fragment Ion m/z | Retention Time [min] | Q1 Pre Bias [V] | Collision Energy [V] | Q3 Pre Bias [V] |
| --- | --- | --- | --- | --- | --- | --- |
| GLEWVGWINTYTGEPTYAADFKR | 892.1 | 1045.5 | 5.211 | -34 | -26 | -40 |
| GLEWVGWINTYTGEPTYAADFKR | 892.1 | 1017 | 5.211 | -34 | -25 | -38 |
| GLEWVGWINTYTGEPTYAADFKR | 892.1 | 924 | 5.211 | -34 | -25 | -34 |
| GLEWVGWINTYTGEPTYAADFKR | 892.1 | 867.4 | 5.211 | -34 | -26 | -32 |
| GLEWVGWINTYTGEPTYAADFKR | 892.1 | 1095 | 5.211 | -34 | -27 | -42 |
| GLEWVGW | 846.4 | 361.2 | 5.396 | -32 | -30 | -26 |
| GLEWVGW | 846.4 | 300.2 | 5.396 | -20 | -36 | -21 |
| GLEWVGW | 846.4 | 486.2 | 5.396 | -34 | -30 | -18 |
| GLEWVGW | 846.4 | 585.3 | 5.396 | -32 | -25 | -30 |
| GLEWVGW | 846.4 | 642.3 | 5.396 | -32 | -25 | -24 |

*Peptide containing "C" is processed with reductive alkylation.

TABLE 6

Peptides for Quantification of Rituximab along with Data for Mass Spectrometry
Solid-phase enzyme: Trypsin TPCK-treated (Sigma-Aldrich)

| Peptide Sequence | Parent Ion m/z | Fragment Ion m/z | Retention Time [min] | Q1 Pre Bias [V] | Collision Energy [V] | Q3 Pre Bias [V] |
| --- | --- | --- | --- | --- | --- | --- |
| ATLTADK | 360.2 | 648.4 | 2.787 | -26 | -14 | -24 |
| ATLTADK | 360.2 | 547.3 | 2.787 | -13 | -13 | -20 |
| ATLTADK | 360.2 | 434.2 | 2.787 | -26 | -16 | -22 |
| ATLTADK | 360.2 | 333.2 | 2.787 | -26 | -19 | -24 |
| ATLTADK | 360.2 | 262.1 | 2.787 | -13 | -21 | -29 |
| VTMTCR | 384.2 | 668.3 | 2.868 | -28 | -16 | -34 |
| VTMTCR | 384.2 | 567.2 | 2.868 | -28 | -14 | -40 |
| VTMTCR | 384.2 | 436.2 | 2.868 | -28 | -16 | -16 |
| VTMTCR | 384.2 | 335.1 | 2.868 | -14 | -17 | -23 |
| VTMTCR | 384.2 | 201.1 | 2.868 | -28 | -14 | -21 |
| NMHWVK | 407.7 | 700.4 | 3.163 | -30 | -18 | -26 |
| NMHWVK | 407.7 | 569.3 | 3.163 | -30 | -16 | -30 |
| NMHWVK | 407.7 | 432.3 | 3.163 | -15 | -19 | -16 |
| NMHWVK | 407.7 | 246.2 | 3.163 | -15 | -17 | -28 |
| NMHWVK | 407.7 | 285.2 | 3.163 | -30 | -16 | -20 |
| TSNPPTFGGGTK | 582.3 | 975.5 | 3.287 | -22 | -21 | -38 |
| TSNPPTFGGGTK | 582.3 | 488.2 | 3.287 | -22 | -17 | -17 |
| TSNPPTFGGGTK | 582.3 | 861.4 | 3.287 | -22 | -21 | -32 |
| TSNPPTFGGGTK | 582.3 | 431.2 | 3.287 | -22 | -22 | -16 |
| TSNPPTFGGGTK | 582.3 | 764.4 | 3.287 | -22 | -23 | -40 |

TABLE 6-continued

Peptides for Quantification of Rituximab along with Data for Mass Spectrometry
Solid-phase enzyme: Trypsin TPCK-treated (Sigma-Aldrich)

| Peptide Sequence | Parent Ion m/z | Fragment Ion m/z | Retention Time [min] | Q1 Pre Bias [V] | Collision Energy [V] | Q3 Pre Bias [V] |
|---|---|---|---|---|---|---|
| TSNPPTFGGGTK | 582.3 | 382.7 | 3.287 | -22 | -26 | -27 |
| TSNPPTFGGGTK | 582.3 | 419.2 | 3.287 | -22 | -34 | -30 |
| LASGVPVR | 399.7 | 685.4 | 3.375 | -29 | -17 | -34 |
| LASGVPVR | 399.7 | 614.4 | 3.375 | -30 | -16 | -32 |
| LASGVPVR | 399.7 | 527.3 | 3.375 | -15 | -16 | -38 |
| LASGVPVR | 399.7 | 371.2 | 3.375 | -15 | -17 | -28 |
| ATSNLASGVPVR | 586.3 | 999.6 | 3.687 | -22 | -24 | -38 |
| ATSNLASGVPVR | 586.3 | 798.5 | 3.687 | -22 | -25 | -40 |
| ATSNLASGVPVR | 586.3 | 685.4 | 3.687 | -22 | -22 | -36 |
| ATSNLASGVPVR | 586.3 | 614.4 | 3.687 | -22 | -24 | -32 |
| ATSNLASGVPVR | 586.3 | 527.3 | 3.687 | -22 | -22 | -38 |
| ATSNLASGVPVR | 586.3 | 470.3 | 3.687 | -40 | -19 | -24 |
| ATSNLASGVPVR | 586.3 | 371.2 | 3.687 | -22 | -19 | -13 |
| ATSNLASGVPVR | 586.3 | 801.4 | 3.687 | -22 | -16 | -30 |
| SQSPAILSASPGEK | 686.4 | 1156.6 | 3.77 | -26 | -24 | -44 |
| SQSPAILSASPGEK | 686.4 | 1069.6 | 3.77 | -26 | -22 | -40 |
| SQSPAILSASPGEK | 686.4 | 535.3 | 3.77 | -26 | -24 | -38 |
| SQSPAILSASPGEK | 686.4 | 901.5 | 3.77 | -26 | -29 | -26 |
| SQSPAILSASPGEK | 686.4 | 788.4 | 3.77 | -26 | -26 | -30 |
| SQSPAILSASPGEK | 686.4 | 675.3 | 3.77 | -26 | -28 | -26 |
| STSGGTAALGCLVK | 661.3 | 1046.6 | 4.087 | -40 | -24 | -40 |
| STSGGTAALGCLVK | 661.3 | 989.5 | 4.087 | -40 | -24 | -38 |
| STSGGTAALGCLVK | 661.3 | 932.5 | 4.087 | -40 | -24 | -36 |
| STSGGTAALGCLVK | 661.3 | 831.5 | 4.087 | -40 | -25 | -32 |
| STSGGTAALGCLVK | 661.3 | 760.4 | 4.087 | -40 | -25 | -28 |
| STSGGTAALGCLVK | 661.3 | 689.4 | 4.087 | -40 | -24 | -36 |
| STSGGTAALGCLVK | 661.3 | 576.3 | 4.087 | -40 | -23 | -30 |
| FSGSGSGTSYSLTISR | 803.9 | 1084.6 | 4.015 | -30 | -32 | -42 |
| FSGSGSGTSYSLTISR | 803.9 | 926.5 | 4.015 | -30 | -34 | -36 |
| FSGSGSGTSYSLTISR | 803.9 | 839.5 | 4.015 | -30 | -36 | -32 |
| FSGSGSGTSYSLTISR | 803.9 | 676.4 | 4.015 | -30 | -33 | -26 |
| FSGSGSGTSYSLTISR | 803.9 | 589.4 | 4.015 | -30 | -34 | -22 |
| FSGSGSGTSYSLTISR | 803.9 | 476.3 | 4.015 | -30 | -32 | -17 |
| FSGSGSGTSYSLTISR | 803.9 | 375.2 | 4.015 | -30 | -33 | -27 |
| IYATSNLASGVPVR | 724.4 | 999.6 | 4.125 | -40 | -28 | -38 |
| IYATSNLASGVPVR | 724.4 | 685.4 | 4.125 | -40 | -29 | -26 |

TABLE 6-continued

Peptides for Quantification of Rituximab along with Data for Mass Spectrometry
Solid-phase enzyme: Trypsin TPCK-treated (Sigma-Aldrich)

| Peptide Sequence | Parent Ion m/z | Fragment Ion m/z | Retention Time [min] | Q1 Pre Bias [V] | Collision Energy [V] | Q3 Pre Bias [V] |
|---|---|---|---|---|---|---|
| IYATSNLASGVPVR | 724.4 | 614.4 | 4.125 | -40 | -26 | -32 |
| IYATSNLASGVPVR | 724.4 | 527.3 | 4.125 | -40 | -25 | -40 |
| IYATSNLASGVPVR | 724.4 | 371.2 | 4.125 | -40 | -22 | -27 |
| IYATSNLASGVPVR | 724.4 | 1077.6 | 4.125 | -40 | -19 | -42 |
| GPSVFPLAPSSK | 593.8 | 945.5 | 4.372 | -40 | -21 | -36 |
| GPSVFPLAPSSK | 593.8 | 846.5 | 4.372 | -40 | -21 | -32 |
| GPSVFPLAPSSK | 593.8 | 699.4 | 4.372 | -40 | -22 | -36 |
| GPSVFPLAPSSK | 593.8 | 489.3 | 4.372 | -40 | -27 | -25 |
| GPSVFPLAPSSK | 593.8 | 418.2 | 4.372 | -40 | -28 | -30 |
| GPSVFPLAPSSK | 593.8 | 769.4 | 4.372 | -40 | -18 | -30 |
| ASGYTFTSYNMHWVK | 597.9 | 860.9 | 4.392 | -22 | -18 | -32 |
| ASGYTFTSYNMHWVK | 597.9 | 817.4 | 4.392 | -22 | -18 | -30 |
| ASGYTFTSYNMHWVK | 597.9 | 788.9 | 4.392 | -22 | -18 | -30 |
| ASGYTFTSYNMHWVK | 597.9 | 707.3 | 4.392 | -22 | -18 | -26 |
| ASGYTFTSYNMHWVK | 597.9 | 656.8 | 4.392 | -22 | -18 | -24 |
| ASGYTFTSYNMHWVK | 597.9 | 656.8 | 4.392 | -22 | -18 | -24 |
| ASGYTFTSYNMHWVK | 597.9 | 1064.5 | 4.392 | -22 | -24 | -40 |
| ASSSVSYIHWFQQK | 556.6 | 798.9 | 4.338 | -20 | -17 | -30 |
| ASSSVSYIHWFQQK | 556.6 | 755.4 | 4.338 | -20 | -16 | -28 |
| ASSSVSYIHWFQQK | 556.6 | 711.9 | 4.338 | -20 | -19 | -26 |
| ASSSVSYIHWFQQK | 556.6 | 668.3 | 4.338 | -40 | -16 | -24 |
| ASSSVSYIHWFQQK | 556.6 | 618.8 | 4.338 | -20 | -17 | -22 |
| ASSSVSYIHWFQQK | 556.6 | 550.3 | 4.338 | -20 | -14 | -40 |
| ASSSVSYIHWFQQK | 556.6 | 403.2 | 4.338 | -20 | -29 | -25 |
| GLEWIGAIYPGNGDTSYNQK | 728.4 | 792.9 | 5.008 | -28 | -17 | -30 |
| GLEWIGAIYPGNGDTSYNQK | 728.4 | 672.3 | 5.008 | -28 | -16 | -24 |
| GLEWIGAIYPGNGDTSYNQK | 728.4 | 590.8 | 5.008 | -28 | -21 | -22 |
| GLEWIGAIYPGNGDTSYNQK | 728.4 | 740.4 | 5.008 | -28 | -27 | -28 |
| GLEWIGAIYPGNGDTSYNQK | 728.4 | 840.5 | 5.008 | -28 | -16 | -32 |

*Peptide containing "C" is processed with reductive alkylation.

Example 2: Study 1 on Filtration Membrane

To study peptide recovery rates when different membrane materials are used for filtration, two membrane materials—polytetrafluoroethylene (PTFE) and polyvinylidene difluoride (PVDF)—were compared.

Figures 1, 2:
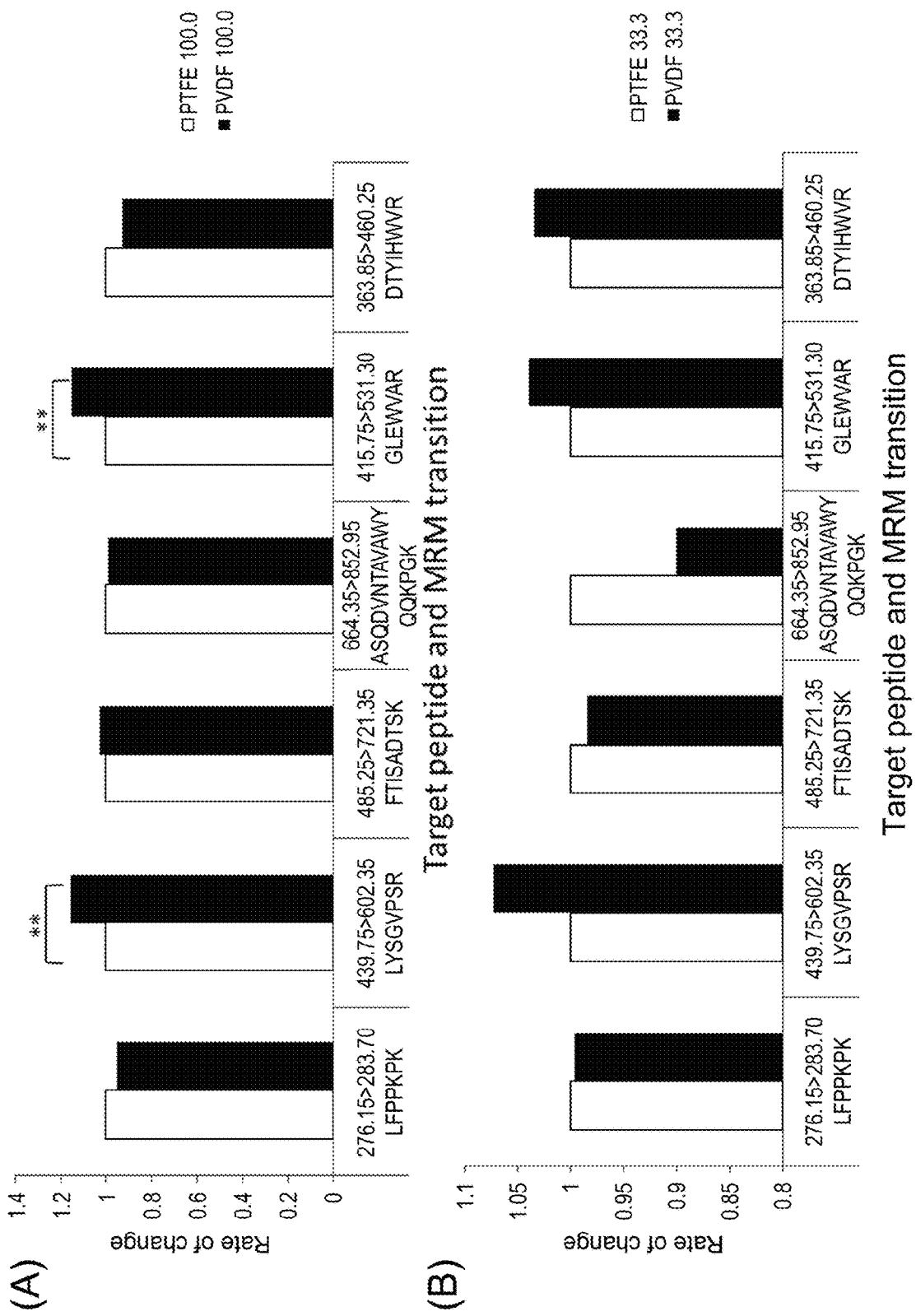
Figure 2:
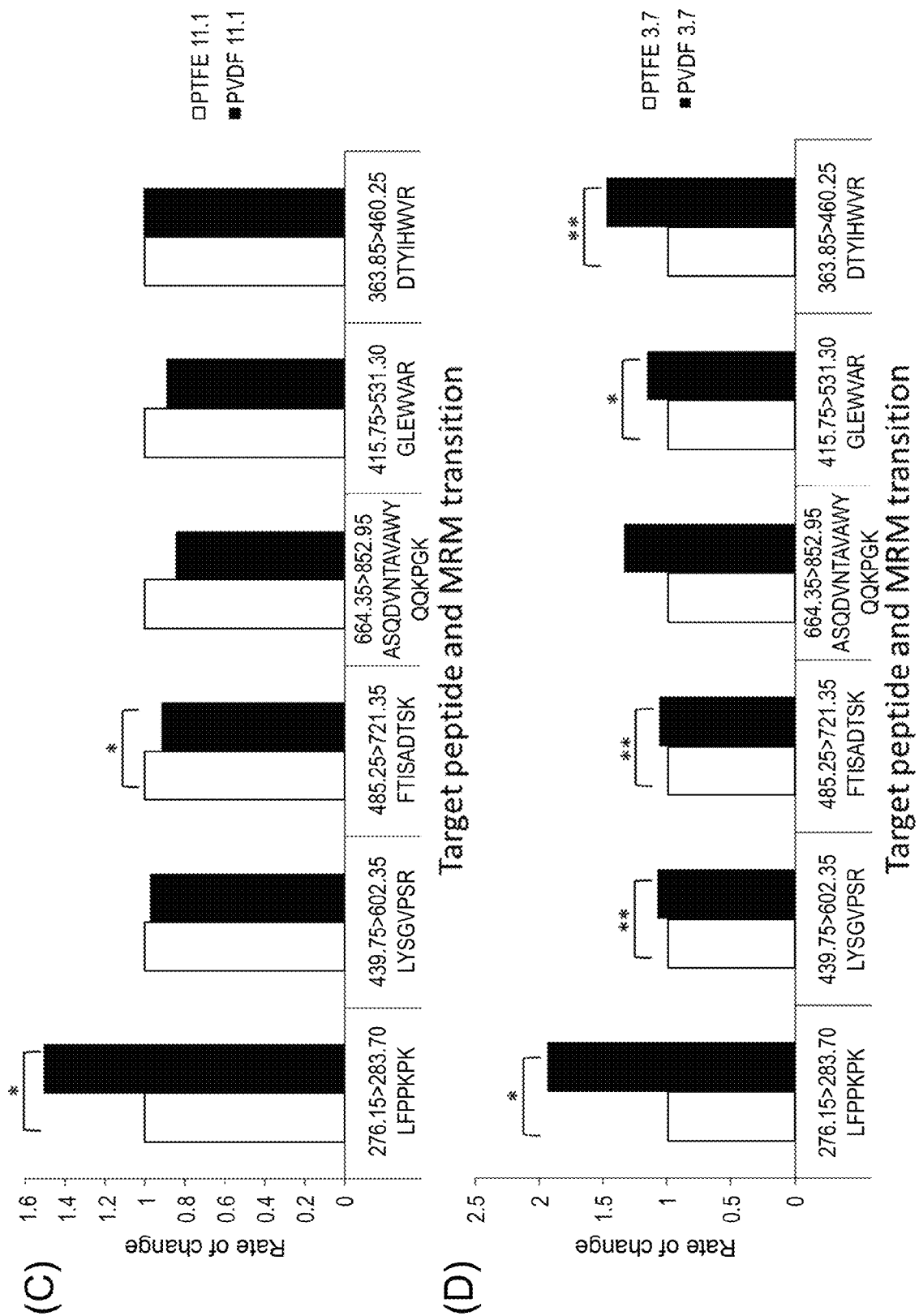
Figures 2, 3:
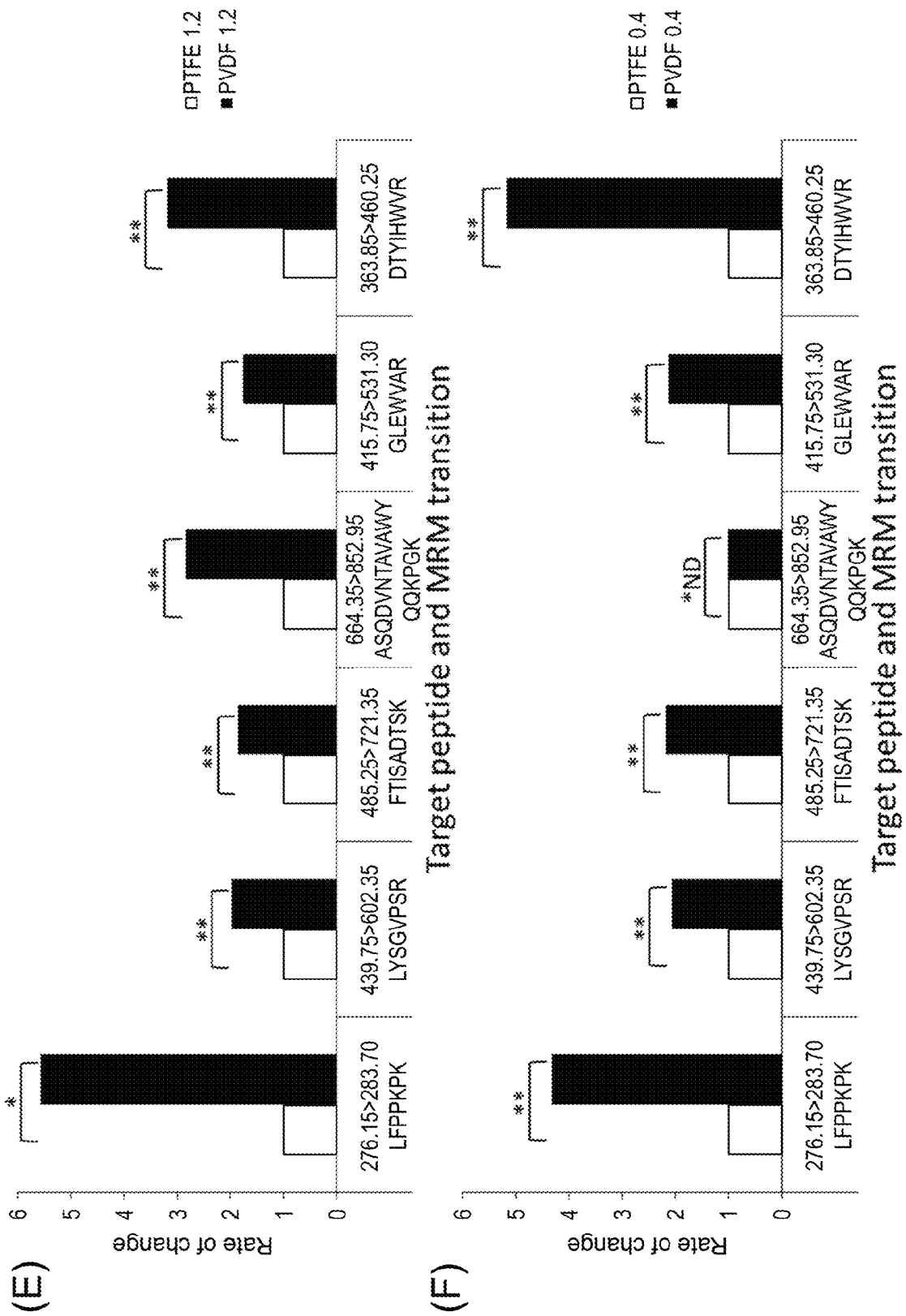
Figure 3:
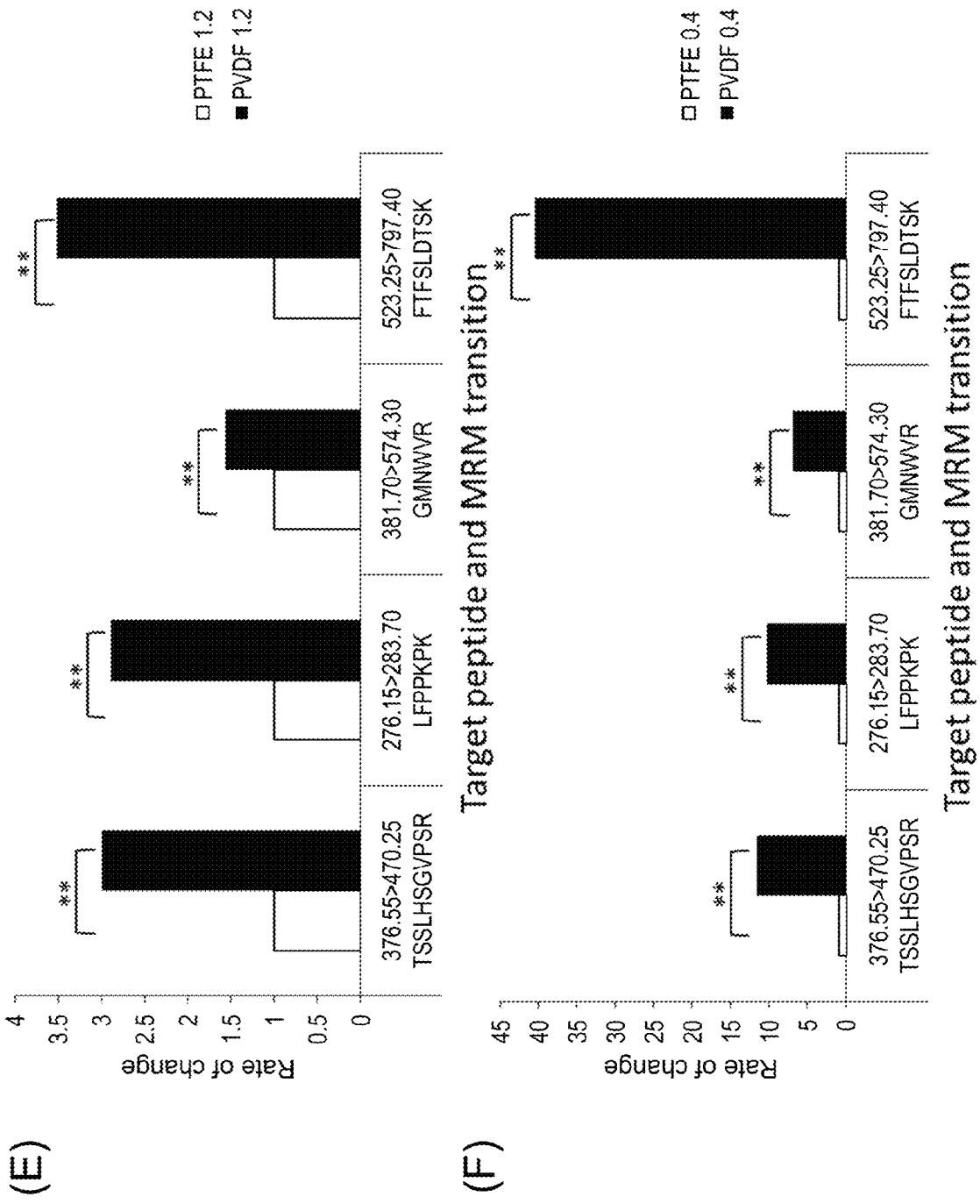

The study on peptide recovery rates started with 100 μg/mL trastuzumab, which was then diluted by 3-fold serial dilution (N=4). Protease reaction was performed using nanoparticles with immobilized trypsin (Trypsin TPCK treated). Then, relative to peptides with known sequences (LFPPKPK (SEQ ID NO: 46), LYSGVPSR (SEQ ID NO: 21), FTISADTSK (SEQ ID NO: 3), ASQDVNTAVAWYQQKPGK (SEQ ID NO: 47), GLEWVAR (SEQ ID NO: 6), DTYIHWVR (SEQ ID NO: 5)), recovered peptides were quantified through mass spectrometry (LCMS-8040, Shimadzu Corporation). FIG. 2-1 through FIG. 2-3 show the recovery results of PVDF relative to those of PRFE (rate of variation). In significant difference testing, T-test was employed; (*) was marked for p<0.05 and (**) for p<0.01.

As a result, no difference in the results was observed among high-concentration peptides, whereas a significant difference was evident in the recovery rates among low-concentration peptides. Accordingly, PVDF was found to be suitable as a filtration membrane.

Example 3: Study 2 on Filtration Membrane

The same test as in Example 2 was conducted using bevacizumab. The results are shown in FIG. 3-1 through FIG. 3-3.

As a result, the same as in Example 2, no difference in the results was observed in recovery rates among high-concentration peptides, whereas a significant difference was evident in the recovery rates among low-concentration peptides. Accordingly, PVDF was found to be suitable as a filtration membrane.

Example 4: Study 3 on Filtration Membrane

To study peptide recovery rates when filtration membrane plates are used for detection of multiple samples, two membrane materials (PTFE, PVDF) and three types of housing were compared. Multiscreen plates were used for comparison—1) PTFE membrane/Solvinert housing (Merck), 2) PVDF membrane/Acryl clear housing (Merck), 3) PVDF membrane/Barex white housing (Merck).

Figure 4:
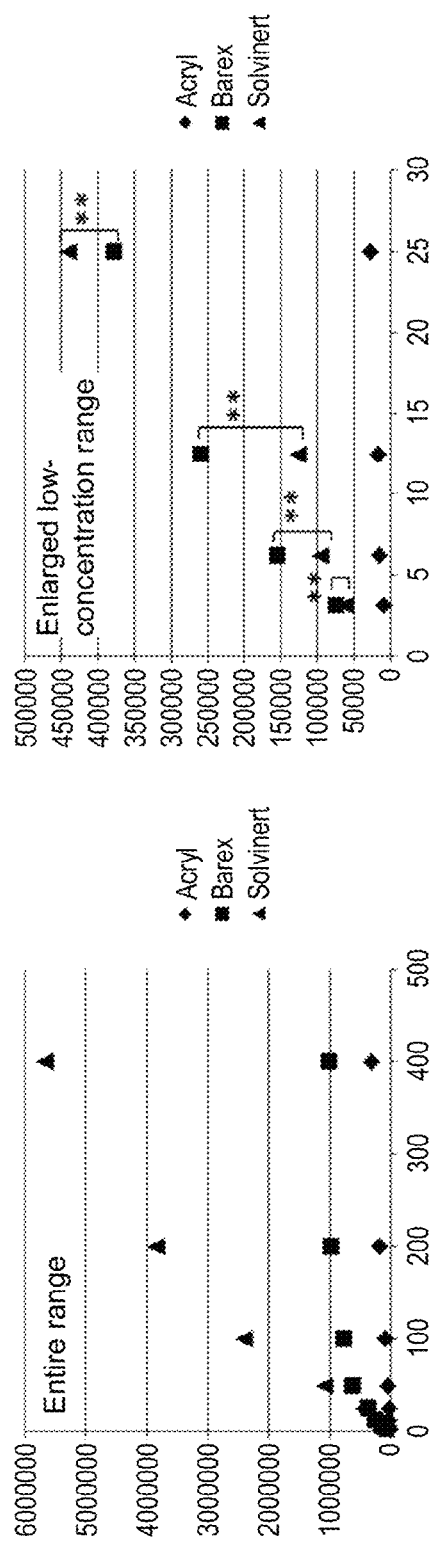
Figure 1:
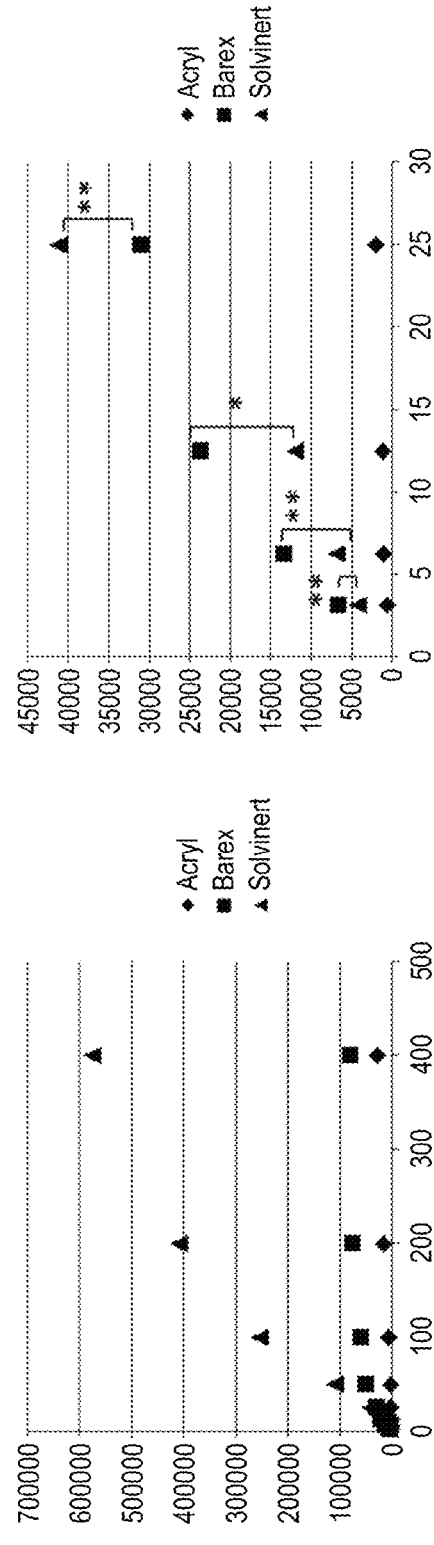
Figure 4:
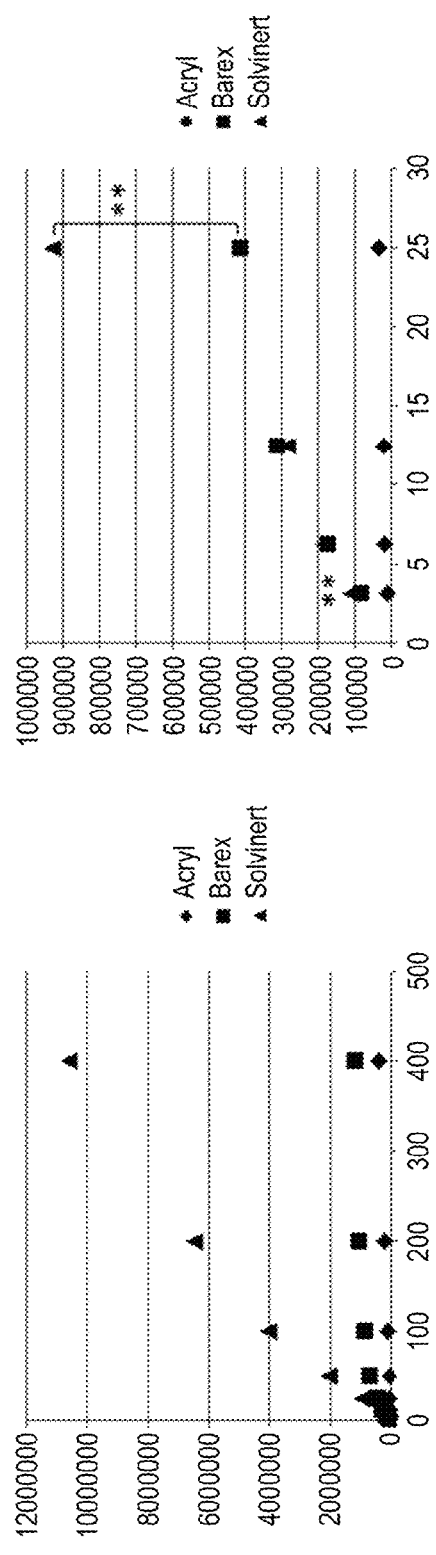
Figure 2:
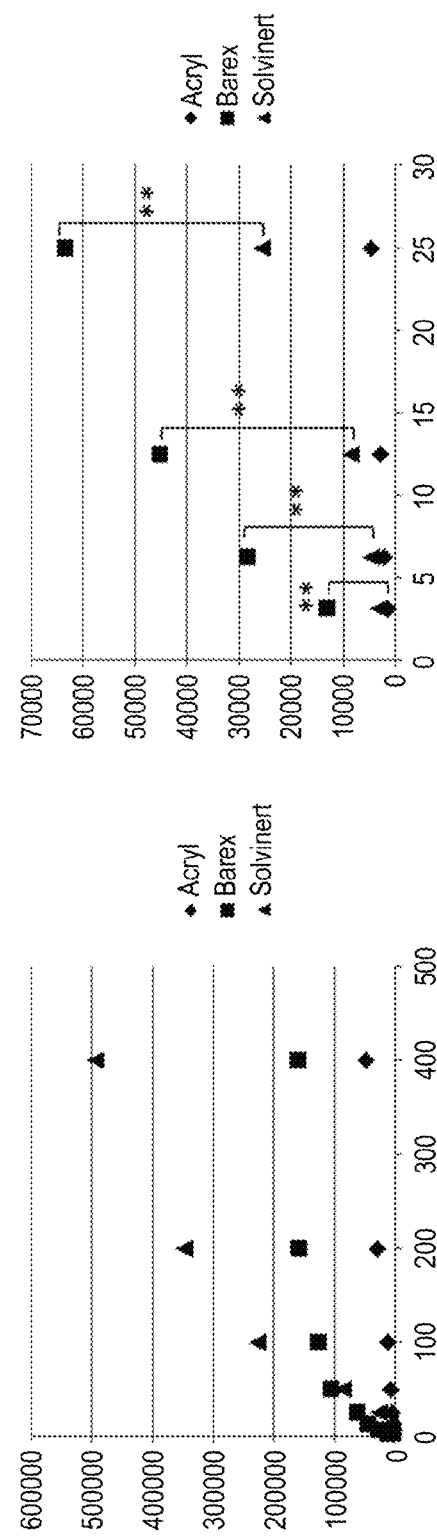

The study on peptide recovery rates started with 400 µg/mL of trastuzumab, which was diluted by 2-fold serial dilution (N=4). After proteolysis was performed, recovered peptides were quantified through mass spectrometry (LCMS-8040) relative to each of the known peptides. The results are shown in FIG. 4-1 through FIG. 4-2. In significant difference testing, T-test was employed; (*) was marked for p<0.05 and (**) for p<0.01.

Accordingly, it was found that PTFE had better results among high-concentration peptides, whereas PVDF showed better results among low-concentration peptides. Since clinically required peptide concentration ranges are 5-20 µg/mL, using PFDV Barex was determined to be effective. When Barex resin was used, peptide saturation was observed at high-concentration ranges. It was thought to be caused by agglomeration of protein components. Since blood samples contain a large amount of antibodies and are washed by a surfactant in clinical settings, any saturation phenomenon is thought to be eliminated. Note that acrylic resins caused a large amount of peptide loss due to physical adsorption and were excluded from consideration.

Example 5: Assessment of Stability of Protease Activity

To monitor the stability of protease (trypsin) activity immobilized on nanoparticles, the enzyme activity was measured. Since nanoparticles inhibit substrate absorbance, some modifications were made on conventional procedures.

To examine enzyme stability, enzymatic reactions were carried out under various conditions using two types of trypsin as proteases—Trypsin Gold Mass Spec Grade (Promega) (hereinafter referred to as "Gold") and Trypsin TPCK-treated from bovine pancreas, Product Number T1426, (Sigma Aldrich) (hereinafter referred to as "TPCK") as well as "FG-Gold" and "FG-TPCK" prepared respectively by immobilizing "Gold" and "TPCK" on nanoparticles using a kit described in Example 1. Note that "Gold" is a mass-spectrometry grade protease, which has been subjected to a reductive dimethyl reaction in addition to chymotrypsin inactivation (TPCK-treated), and which has resistance to autolysis and maintains highly broad activity regardless of temperature or pH; and "TPCK" is a protease on which chymotrypsin remains even after being processed with chymotrypsin-inactivation treatment.

As the substrate, N-α-benzoyl-DL-arginine-p-nitroanilide hydrochloride (MW=434.9) was used. Enzyme activities were determined by measuring the absorbance of p-nitroaniline (p-NA) isolated from the substrate by hydrolysis (405 nm, absorption coefficient=9920 $M^{-1} \cdot cm^{-1}$).

<Protocol>

The protease substrate is dissolved in DMSO to form a stock solution having a final concentration of 10 mM, which is then mixed as follows.

substrate: 10 µL (100 nmol)
reaction buffer (50 mM Tris-HCl, 150 mM NaCl, pH 8.0): 200 µL
suspension of immobilized enzyme (0.5 mg/mL): 2 µL To compensate for the absorbance of suspended nanoparticles (FG beads) themselves and the loss of FG beads due to their physical adsorption to wall surfaces, sample wells without the substrate are prepared as a control, which are subjected to simultaneous measurement. Each sample (N=2) is measured, and the average value is set as its absorbance. FG beads are well suspended before being added.

Under each condition, protease reactions were carried out for 1.5 hours using a vortex mixer. The reaction was completely terminated by adding 50 mL of 2N—HCl. The reaction mixture was filtered using a multiscreen filter plate (Millipore MultiScreen PVDF, Barex, 0.2 µm). After nanoparticles were removed, the mixture was dispensed into an optical bottom plate (Cosmo Bio Co., Ltd.). Using a microplate reader (TECAN Infinite M200 Pro, Tecan Japan), enzyme activities were assessed by measuring the absorbance of p-nitroaniline (p-NA) isolated from the substrate by hydrolysis (405 nm, absorption coefficient=9920 $M^{-1} \cdot cm^{-1}$).

At room temperature of 25° C., the absorbance was measured continuously 120 times every minute directly after vortex mixing. An approximate straight line was created following an increase in absorbance, and its inclination was set as the enzyme kinetics.

Figure 5:
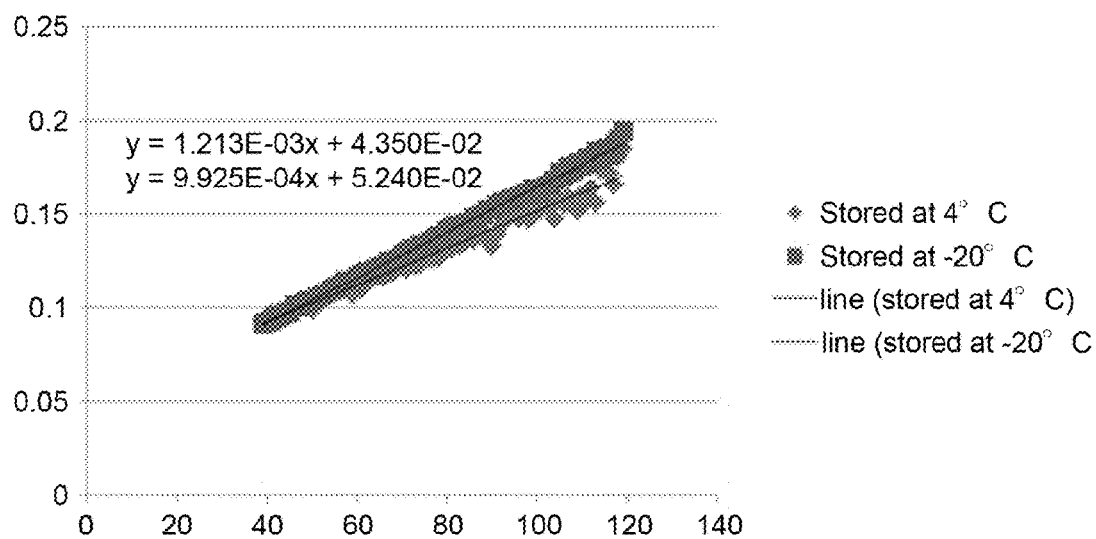
FIG. 5 shows chronological change in the stability of nanoparticles used in the method related to the present invention: (A) absorbance of p-nitroaniline that increases when the substrate of trypsin is cleaved, vertical axis set for absorbance at 405 nm and the horizontal axis for reaction time (min.); and (B) enzyme activity.
Figure 5:
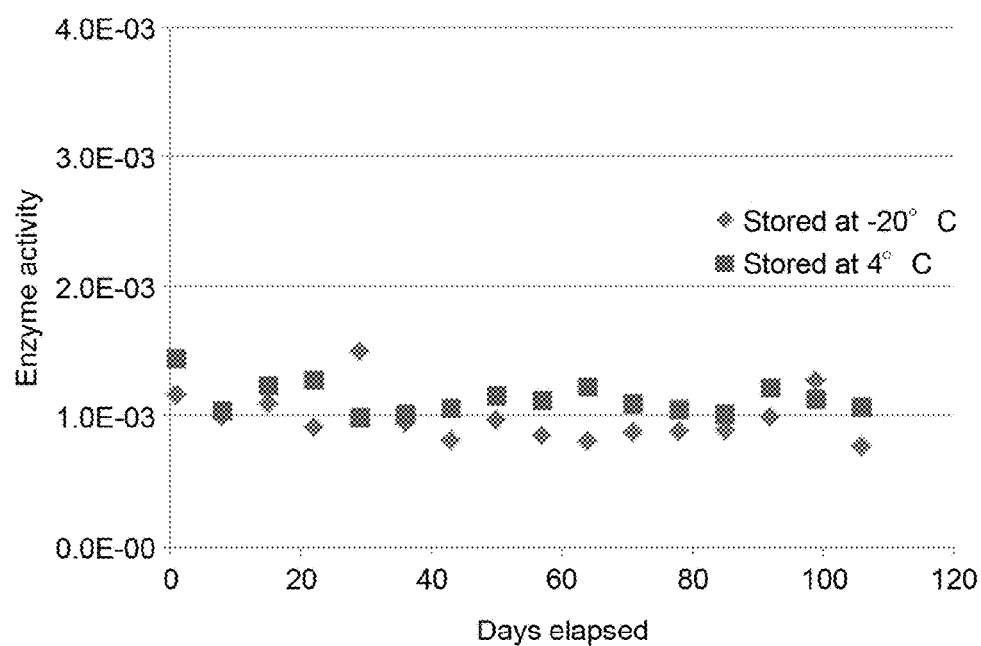

Nanoparticles with immobilized trypsin were stored at 4° C. and −20° C. respectively, and their enzyme activities were monitored for approximately 3 months for evaluation. As shown in FIG. 5, storage stability was not affected by temperatures. Accordingly, it was found that storing at 4° C. is sufficient when a kit is provided.

Example 6: Assessment of Scale-Up

In mass production of nanoparticles with immobilized protease, whether or not change is observed in protease activity was studied. For measurement, the same modification as in Example 5 was made, except that the reaction buffer was replaced with 50 mM Tris-HCl, pH 8.0.

Figure 6:
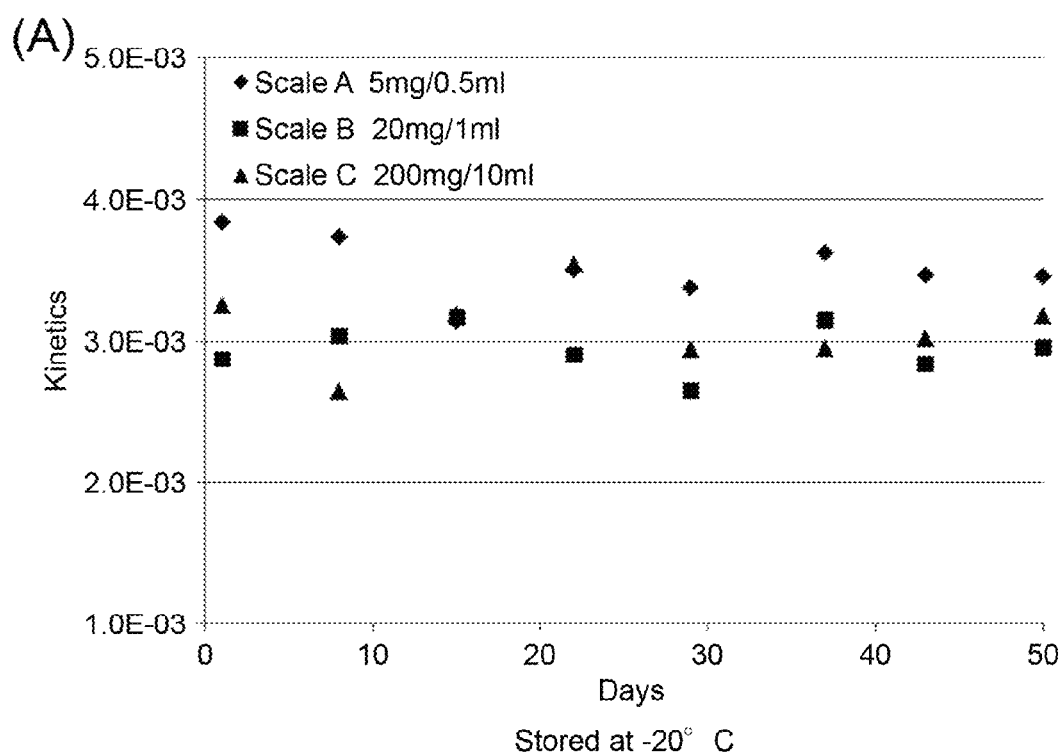
FIG. 6 shows chronological change in stability of nanoparticles used in the method related to the present invention: (A) results when stored at −20° C. and (B) results when stored at 4° C.
Figure 6:
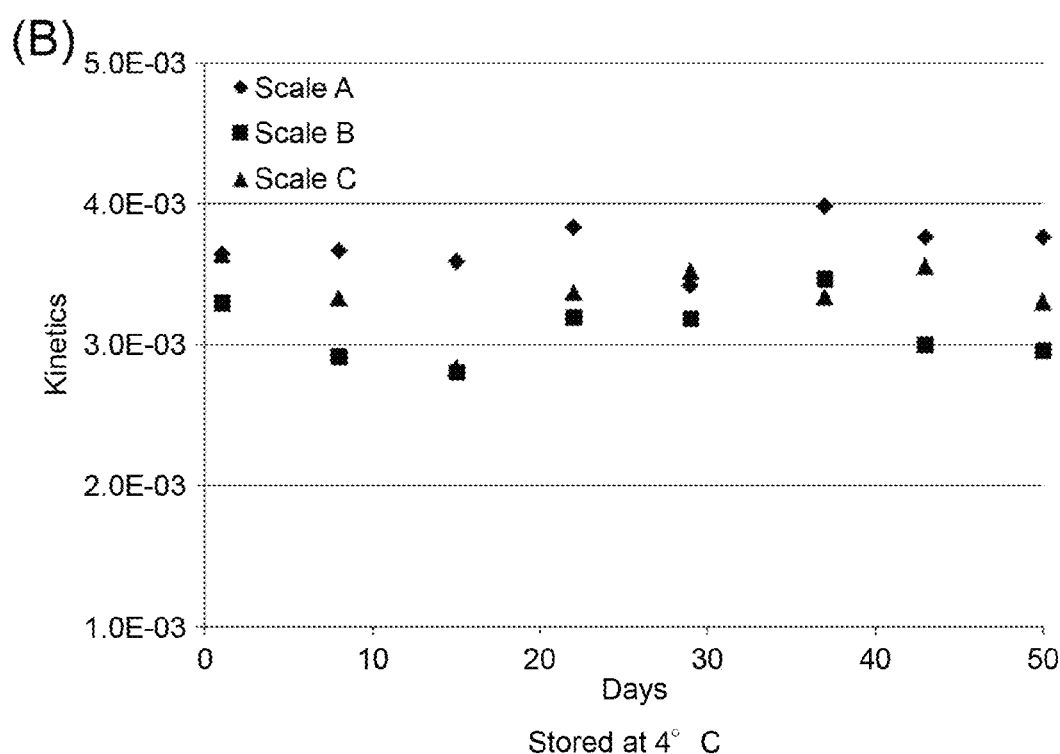

For comparison, the initial amounts of nanoparticles to be introduced were set as a lab scale (Scale A, 5 mg), millimeter-gram scale (Scale B, 20 mg) and large scale (Scale C, 200 mg). Enzyme activities were monitored for about two months. The results are shown in FIG. 6.

As a result, it was found that there was no decrease in enzyme activity caused by scaled-up production.

Example 7: Assessment of Scale-Up

In mass production of nanoparticles, a washing step may be insufficient. To enhance the efficiency of a washing step, a surfactant was used as the washing solution after nanoparticles were immobilized and the effect was studied.

When enzyme activities were assessed, the results are as follows:

without masking (detergent −) FG beads trypsin: 5.784E-03 with masking (detergent +) FG beads trypsin: 5.902E-03

Accordingly, it was determined that there was no occurrence of enzyme inactivity caused by surfactant washing.

INDUSTRIAL APPLICABILITY

Using a kit related to the present invention simplifies the identification/quantification of a monoclonal antibody in a sample, while reducing the error in procedures. Moreover, since the ionic species of interest have been already determined, setting mass spectrometry conditions is not required for users.

Especially, techniques for determining concentration through mass spectrometry have a potential to replace the current ELISA technique. The present invention contributes to advancement in clinical pharmacology and market expansion.

All publications, patents and patent applications cited herein are incorporated in the present application.

The invention claimed is:

1. A method for preparing a sample for detection of a monoclonal antibody through high-performance liquid chromatography-mass spectrometry, comprising:
providing porous bodies having pores and a target monoclonal antibody immobilized in the pores of the porous bodies, and nanoparticles having an immobilized protease;
bringing the porous bodies and the nanoparticles into contact with each other in a buffer in a reaction vessel comprising a filtration membrane such that the target monoclonal antibody in the porous bodies and the immobilized protease on the nanoparticles undergo a selective protease proteolysis reaction in the reaction vessel; and
applying pressure or centrifugal force to the reaction vessel containing the buffer such that the buffer and digested peptide fragments produced through the protease proteolysis reaction permeate through the filtration membrane and that the filtration membrane prevents permeation of the porous bodies and the nanoparticles,
wherein the filtration membrane has a pore size set in a range that allows permeation of the digested peptide fragments produced through the protease proteolysis reaction and prevents the permeation of the porous bodies and the nanoparticles.

2. The method according to claim 1, wherein the filtration membrane comprises polyvinylidene difluoride.

3. The method according to claim 1, wherein the target monoclonal antibody is trastuzumab, trastuzumab-DM1, bevacizumab or rituximab.

4. The method according to claim 1, wherein the nanoparticles have an average particle size that is greater than an average pore size of the pores in the porous bodies.

5. The method according to claim 1, wherein the porous bodies have the pores having an average pore diameter in a range of 10 mm to 200 nm.

6. The method according to claim 1, wherein the nanoparticles have an average particle size in a range of 50 nm to 500 nm.

7. The method according to claim 1, wherein the nanoparticles have an average particle size that is at least 1.2 times an average pore size of the pores in the porous bodies.

8. The method according to claim 1, wherein the nanoparticles have an average particle size that is in a range of 50 nm to 500 nm and at least 1.2 times an average pore size of the pores in the porous bodies.

9. The method according to claim 1, wherein the porous bodies have linker molecules immobilized in the pores of the porous body such that the linker molecules make site-specific bonding with Fe domains of antibodies, and the selective protease proteolysis reaction is regioselective digestion reaction of Fab domain by the immobilized protease on the nanoparticles.

10. The method according to claim 1, wherein the pore size of the filtration membrane is set such that the buffer and the digested peptide fragments produced through the protease reaction do not permeate through the filtration membrane without application of the pressure or the centrifugal force.

11. The method according to claim 2, wherein the target monoclonal antibody is trastuzumab, trastuzumab-DM1, bevacizumab or rituximab.

12. The method according to claim 2, wherein the nanoparticles have an average particle size that is greater than an average pore size of the pores in the porous bodies.

13. The method according to claim 2, wherein the porous bodies have the pores having an average pore diameter in a range of 10 nm to 200 nm.

14. The method according to claim 2, wherein the nanoparticles have an average particle size in a range of 50 nm to 500 mm.

15. The method according to claim 2, wherein the nanoparticles have an average particle size that is at least 1.2 times an average pore size of the pores in the porous bodies.

16. The method according to claim 2, wherein the nanoparticles have an average particle size that is in a range of 50 nm to 500 nm and at least 1.2 times an average pore size of the pores in the porous bodies.

17. The method according to claim 2, wherein the porous bodies have linker molecules immobilized in the pores of the porous body such that the linker molecules make site-specific bonding with Fe domains of antibodies, and the selective protease proteolysis reaction is regioselective digestion reaction of Fab domain by the immobilized protease on the nanoparticles.

18. The method according to claim 3, wherein the nanoparticles have an average particle size that is greater than an average pore size of the pores in the porous bodies.

19. The method according to claim 3, wherein the porous bodies have the pores having an average pore diameter in a range of 10 nm to 200 nm.

20. The method according to claim 3, wherein the nanoparticles have an average particle size in a range of 50 nm to 500 nm.

* * * * *